US009408535B2

(12) United States Patent
Mowrey et al.

(10) Patent No.: US 9,408,535 B2
(45) Date of Patent: Aug. 9, 2016

(54) PHOTOREFRACTION OCULAR SCREENING DEVICE AND METHODS

(71) Applicant: Welch Allyn, Inc., Skaneateles Falls, NY (US)

(72) Inventors: Richard Allen Mowrey, Ottawa (CA); Martin Edson Rivers, Kanata (CA); Rejean Joseph Yvon Bruno Munger, Ottawa (CA)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/963,332

(22) Filed: Dec. 9, 2015

(65) Prior Publication Data

US 2016/0089021 A1 Mar. 31, 2016

Related U.S. Application Data

(62) Division of application No. 13/399,682, filed on Feb. 17, 2012, now Pat. No. 9,237,846.

(60) Provisional application No. 61/443,871, filed on Feb. 17, 2011.

(51) Int. Cl.
*A61B 3/10* (2006.01)
*A61B 3/103* (2006.01)
*A61B 3/00* (2006.01)
*A61B 5/00* (2006.01)
(Continued)

(52) U.S. Cl.
CPC .............. *A61B 3/103* (2013.01); *A61B 3/0025* (2013.01); *A61B 3/14* (2013.01); *A61B 3/158* (2013.01); *A61B 5/725* (2013.01); *A61B 5/7246* (2013.01)

(58) Field of Classification Search
CPC ...... A61B 3/0008; A61B 3/103; A61B 3/107; A61B 3/113; A61B 3/158; G02C 7/028
USPC .......................... 351/205, 206, 210, 221, 246
See application file for complete search history.

(56) References Cited

U.S. PATENT DOCUMENTS

| 3,602,580 A | 8/1971 | Samuels |
| 3,879,113 A | 4/1975 | Howland et al. |
| 4,523,820 A | 6/1985 | Kaakinen |

(Continued)

FOREIGN PATENT DOCUMENTS

| EP | 0962184 | 12/1999 |
| EP | 1308128 | 5/2003 |

OTHER PUBLICATIONS

International Search Report for PCT/US12/1225665 dated Aug. 31, 2012.

*Primary Examiner* — Huy K Mai
(74) *Attorney, Agent, or Firm* — Merchant & Gould P.C.

(57) ABSTRACT

A photorefraction ocular screening device for assessing vision and corresponding disorders associated with the human ocular system is provided. More specifically, the present invention provides for a photorefraction ocular screening device employing advanced methods of pupil detection and refractive error analysis. The photorefraction ocular screening device is comprised of an LED arrangement configured with a plurality of irradiation sources serving as visual stimuli, wherein the visual stimuli may be presented in varying illumination patterns to the pupils of an examinee for expanding the range of ocular responses that can be used to determine refractive error.

13 Claims, 25 Drawing Sheets

(51) Int. Cl.
*A61B 3/14* (2006.01)
*A61B 3/15* (2006.01)

(56) References Cited

U.S. PATENT DOCUMENTS

| | | | |
|---|---|---|---|
| 4,586,796 A | 5/1986 | Molteno | |
| 4,669,836 A | 6/1987 | Richardson et al. | |
| 4,758,080 A | 7/1988 | Howland | |
| 4,834,528 A | 5/1989 | Howland et al. | |
| 4,950,069 A | 8/1990 | Hutchinson | |
| 4,989,968 A | 2/1991 | Freedman | |
| 5,214,456 A | 5/1993 | Gersten | |
| 5,355,895 A | 10/1994 | Hay | |
| 5,502,520 A | 3/1996 | Cibis et al. | |
| 5,632,282 A | 5/1997 | Hay et al. | |
| 5,790,235 A | 8/1998 | Kirschbaum | |
| 5,859,686 A | 1/1999 | Aboutalib et al. | |
| 5,989,194 A | 11/1999 | Davenport et al. | |
| 6,027,216 A | 2/2000 | Guyton et al. | |
| 6,089,715 A | 7/2000 | Hoover et al. | |
| 6,095,989 A | 8/2000 | Hay et al. | |
| 6,325,765 B1 | 12/2001 | Hay et al. | |
| 6,419,638 B1 | 7/2002 | Hay et al. | |
| 6,523,954 B1 | 2/2003 | Kennedy et al. | |
| 6,595,641 B1 | 7/2003 | Braeuning et al. | |
| 6,616,277 B1 | 9/2003 | Davenport | |
| 6,663,242 B1 | 12/2003 | Davenport | |
| 7,110,582 B1 | 9/2006 | Hay | |
| 7,114,808 B2 | 10/2006 | Lai et al. | |
| 7,374,286 B2 | 5/2008 | Fujieda et al. | |
| 7,427,135 B2 | 9/2008 | Chen et al. | |
| 7,490,940 B2 | 2/2009 | Lai et al. | |
| 7,618,143 B2 | 11/2009 | Clark et al. | |
| 7,677,727 B2 | 3/2010 | Shimizu et al. | |
| 7,798,643 B2 | 9/2010 | Waldorf et al. | |
| 7,850,307 B2 | 12/2010 | Chen | |
| 7,878,652 B2 * | 2/2011 | Chen | A61B 3/0008 351/205 |
| 2008/0212027 A1 | 9/2008 | Shimizu | |
| 2009/0079937 A1 | 3/2009 | Chen et al. | |
| 2009/0115966 A1 | 5/2009 | Waldorf et al. | |
| 2010/0007850 A1 | 1/2010 | Aggarwala | |
| 2010/0149491 A1 | 6/2010 | Chu et al. | |
| 2010/0201944 A1 | 8/2010 | Lewis et al. | |
| 2010/0245765 A1 | 9/2010 | Dyer et al. | |
| 2010/0271595 A1 | 10/2010 | Molebny | |

* cited by examiner

| STIMULUS MERIDIAN | DECENTRATION | AXIS | CONJUGATE |
|---|---|---|---|
| 0° | 1 (6.35mm) | | |
| 0° | 2 (12.70mm) | | |
| 0° | 3 (19.05mm) | | |

FIG. 4B

| STIMULUS MERIDIAN | DECENTRATION | AXIS | CONJUGATE |
|---|---|---|---|
| 60° | 1 (6.35mm) | | |
| 60° | 2 (12.70mm) | | |
| 60° | 3 (19.05mm) | | |

FIG. 4C

| STIMULUS MERIDIAN | DECENTRATION | AXIS | CONJUGATE |
|---|---|---|---|
| 120° | 1 (6.35mm) | | |
| 120° | 2 (12.70mm) | | |
| 120° | 3 (19.05mm) | | |

FIG. 4D

| STIMULUS MERIDIAN | DECENTRATION | AXIS | CONJUGATE |
|---|---|---|---|
| 36.59° | 4<br>(27.68mm) | | |
| 143.41° | 4<br>(27.68mm) | | |

FIG. 5B

Pixel Intensity     Pseudo-Gradient

| Stimulus Meridian | D1 | D2 | D3 | D4 |
|---|---|---|---|---|
| 0° | √ | √ | √ | |
| 60° | √ | √ | √ | |
| 120° | √ | √ | √ | |
| 36.59°/143.41° | | | | √ |
FIG. 17A
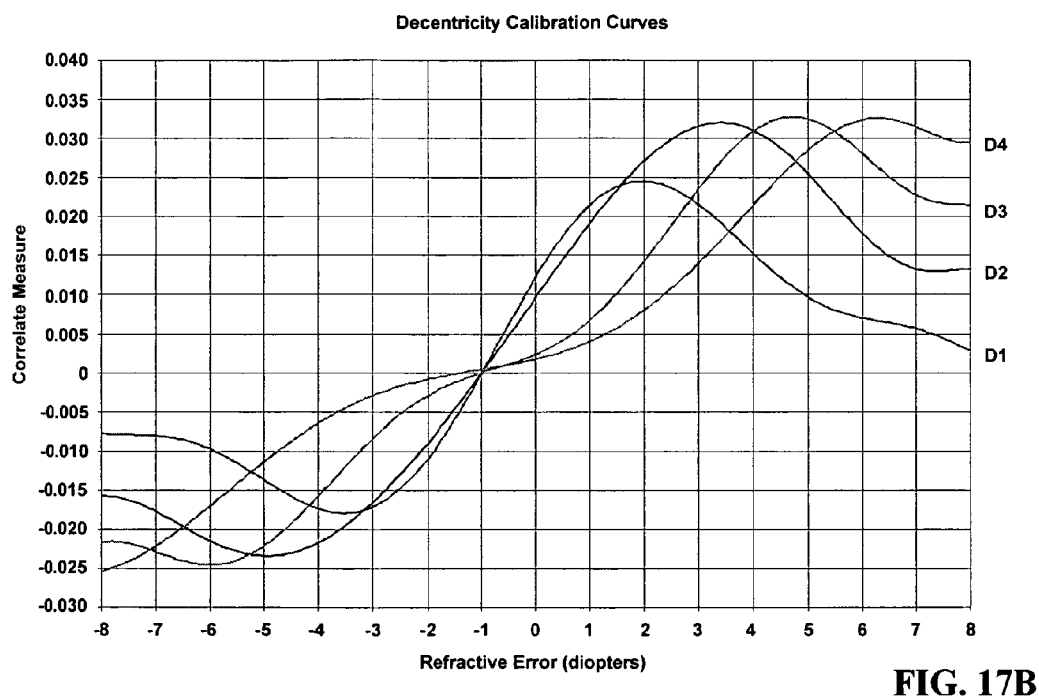
FIG. 17B
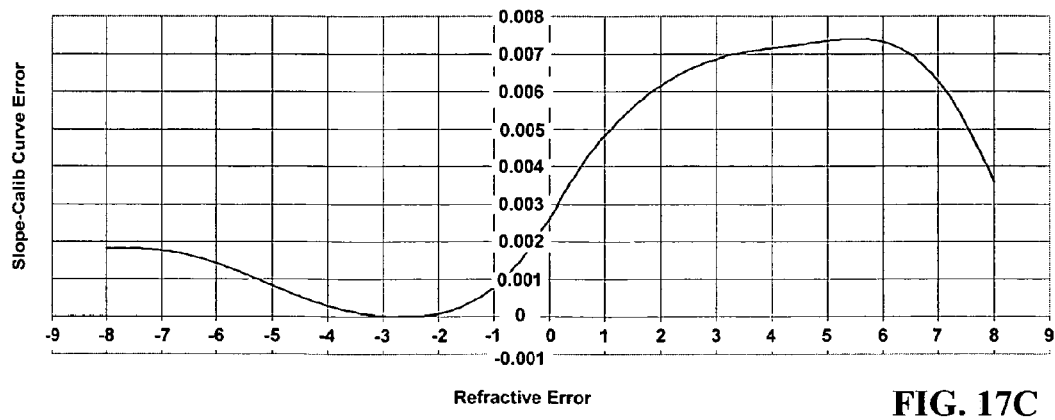
FIG. 17C

PHOTOREFRACTION OCULAR SCREENING DEVICE AND METHODS

TECHNICAL FIELD

The present invention relates generally to the field of ocular examination. More particularly, the present invention is directed to a photorefraction ocular screening device employing novel methods of pupil detection and refractive error analysis for assessing vision and corresponding disorders associated with the human ocular system.

BACKGROUND

The basic function of a photorefractive device is to collect and analyze ocular responses to light stimuli. Light from an external source enters the eye through the pupil and is focused to create a small illuminated spot on the retina. Some of the light from this retinal spot is returned out of the eye through the pupil after interaction with different layers of the retina. The pattern of light exiting the pupil is determined by the optics of the eye and is dominated by an examinee's refractive error (focusing errors of the eye).

Unlike fundus photography, wherein a large area of the retina is illuminated and a camera is focused on the retina to image details of its anatomy, photorefraction does not directly image the retina or any other structures in the posterior segment of the eye. In photorefraction, images are obtained by focusing on the pupil to obtain the light pattern exiting the pupil—i.e., images are analyzed in the pupil plane.

In earlier known methods of photorefraction, typically only eccentric illumination (i.e., lights arranged outside a lens aperture of an ocular screening system) is used. This approach has limitations and can often result in refractive error determinations that are inaccurate or ambiguous, particularly since eyes with different refractive errors can have similar responses under a given illumination. Classic photorefraction using eccentric illumination alone generates a "crescent-like" reflex in the pupil plane, the edges and domains of which must be determined for purposes of correlating the pupil response with a refractive error. When using eccentric or decentered illumination alone, determination of the crescent boundary is a difficult task. In addition, the determination of pupil size and location is often compromised by not having sufficient pupil edge data (due to dark edges) for accurate pupil circle fitting.

Accordingly, there exists a need to provide improved methods of conducting photorefraction-based ocular examinations.

BRIEF DESCRIPTION OF THE DRAWINGS

The objectives and advantages of the present invention will become apparent upon consideration of the following detailed description, taken in conjunction with the accompanying drawings, wherein like reference characters refer to like parts throughout, and in which:

FIG. 17A provides a table of eccentricities associated with stimuli in each of the meridians, and FIGS. 17B-17C are, respectively, exemplary calibration curves for each of eccentricities and a corresponding aggregate calibration error curve to determine refractive error, in accordance with embodiments of the present invention.

DETAILED DESCRIPTION

The present invention is directed to a photorefraction ocular screening device employing methods for ascertaining an examinee's refractive error. For purposes of clarity, and not by way of limitation, illustrative views and process flows of the methods employed in the present invention are described with references made to the earlier identified drawing figures. Various modifications obvious to one skilled in the art are deemed to be within the spirit and scope of the present invention.

Figure 1A:
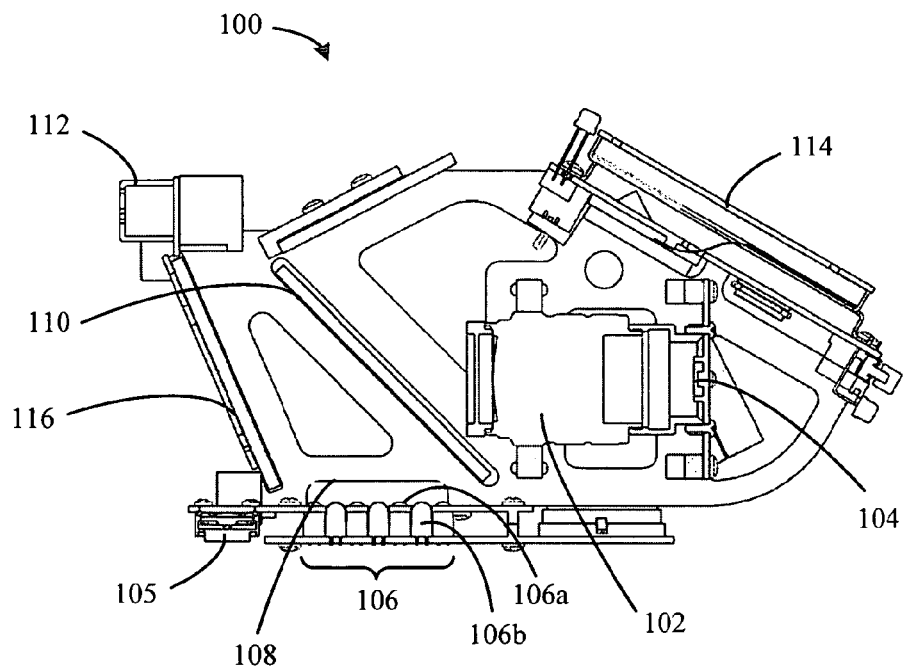
FIGS. 1A and 1B illustrate cross-sectional views of an exemplary photorefraction ocular screening device, in accordance with embodiments of the present invention.
Figure 1B:
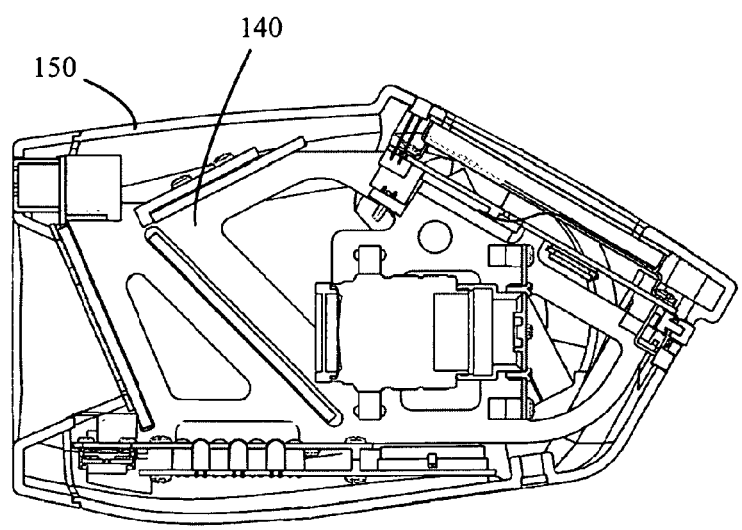

FIGS. 1A and 1B illustrate a cross-sectional view of an exemplary embodiment of a photorefraction ocular screening device 100 for conducting an ocular examination on an examinee. Components of photorefraction ocular screening device 100 are identified and described with reference to FIG. 1A, while FIG. 1B further illustrates a frame 140 enclosed within a housing body 150 of device 100 for supporting the foregoing components identified in FIG. 1A.

Referring to FIG. 1A, device 100 is comprised of optical and non-optical components. Optical components may include a lens component 102 coupled to an image capture component 104, a light-emitting diode (LED) array 106 having visible LEDs 106a and near-infrared LEDs 106b, a holographic diffuser 108 and a beam-splitter 110. Non-optical components may include a speaker 105, a range finder 112, an operator display screen 114 and a front window 116. It should be noted that device 100 is not limited to the foregoing listed components and may incorporate additional components, as deemed necessary, for furthering the processes of the invention described herein.

Device 100 is preferably configured for mobility, but may also be suitable for stationary applications. Additionally, device 100 may be wirelessly enabled to permit image data collection and analysis to be transmitted to a remote location for printing a report or to permit further assessment of an examinee's ocular response. For example, upon conducting an ocular examination using device 100, image data collected and corresponding results may be wirelessly transmitted and stored in a remote patient database configured for accessibility by authorized medical professionals and institutions.

Device 100 functionality is driven by a plurality of processes configured to assess ocular aspects of an examinee including, but not limited to, presenting attention-getting stimuli to the examinee, controlling an LED arrangement to irradiate pupils of the examinee, locating pupils of the examinee in captured images, displaying captured images to an operator, and analyzing pupil image data for determining refractive error and conducting related assessments. These processes may be performed by processing logic (not shown) under computer program control in device 100, which may be comprised of hardware (e.g., circuitry, dedicated logic, programmable logic, microcode, etc.), software (such as instructions run on a processing device), firmware, or a combination thereof.

Attention-Getting Stimuli

Effective ocular screening of cooperative (adults) and non-cooperative (children or animals) examinees may be achieved through the use of device 100. Device 100 may be configured to present attention-getting stimuli to an examinee. The presentation of attention-getting stimuli may be needed, particularly when screening non-cooperative examinees, in order to attract the examinees' direction of gaze. For proper ocular screening, the direction of gaze needs to be in the direction of lens component 102 coupled to image capture component 104 provided in device 100.

Various types of attention-getting stimuli may be utilized. In one embodiment, an auditory stimulus may be used. The auditory stimulus may be a digitally recorded sound track under computer program control in device 100 and may be presented, for example, via speaker 105. In another embodiment, an unfocussed time-dynamic visual stimulus may be used, minimizing an accommodative response from examinees. The visual stimulus may be presented through the use of colored LEDs provided, for example, by LED array 106.

The visual stimulus may be comprised of an arrangement of differently colored LEDs. The arrangement of colored LEDs preferably have wavelengths below 600 nanometers to avoid contamination of near infrared (NIR) LED stimulus, which preferably have a central wavelength of 850 nanometers and are used for purposes of capturing pupil images to conduct an ocular examination. This configuration allows the visual stimulus to be presented for attention getting purposes, but not to be seen in recorded images. The visible LED stimulus is independent of the NIR LED stimulus and is not used in the data analysis associated with determining refractive error or gaze direction. An optimal arrangement of LED array 106 comprises visible LEDs 106a that are positioned between and are coplanar with NIR LEDs 106b. Light emitted by visible LEDs 106a may pass through holographic diffuser 108, creating diffuse stimuli, and is reflected towards the examinee by beam-splitter 110.

As with the auditory stimulus, visible LEDs 106a may also be under computer program control in device 100. More specifically, control parameters such as the intensity, duration, pattern and cycle time associated with visible LEDs 106a may be under computer program control. With respect to intensity, visible LEDs 106a must be regulated to be bright enough to attract the direction of an examinee, while at the same time being limited in brightness to avoid stimulating pupil constriction. The duration of time in which visible LEDs 106a are turned on before being turned off is measured in milliseconds and may be regulated based on the brightness of visible LEDs 106a perceived by the examinee. Visible LEDs 106a may be arranged in a pattern appearing as three concentric rings. In this arrangement, the three concentric rings would appear to the examinee as centered in the image capture component 104 of device 100. Each of the concentric rings may be comprised of more than one LED color spaced apart in a random pattern. A plurality of pattern combinations may be presented to an examinee in random order. The number of data frames collected prior to making a change to a pattern may also be regulated.

The underlying objective of the control parameters associated with visible LEDs 106a is to present diffuse, random and rapidly changing visible light patterns to an examinee. Such patterns are intended to reduce, and in some cases may inhibit, accommodation of the examinee's eyes at a focal distance that is preferably set at one (1) meter from image capture component 104 of device 100. The focal distance may be determined using range finder 112 of device 100. If the eyes of the examinee are capable of full accommodation to a stimulus presented at the 1 meter distance, they will appear to be emmetropic (i.e., needing no optical correction) to device 100. An advantage of the implementation described herein is that, unlike other implementations, accommodation by hyperopes to the 1 meter distance of image capture component 104 of device 100 is diminished, making refractive error determinations for these examinees more accurate.

Presentation of a visual stimulus need not be limited to the use of visible LEDs 106a arranged in LED array 106. In alternate embodiments, the visual stimulus may be provided by an external irradiation source independent of device 100, an external source coupled to and under computer program control of device 100, or other suitable combinations thereof. Regardless of the attention-getting mechanism employed, an attention-getting stimulus is preferably presented continuously throughout an ocular examination.

NIR LED Stimuli

Figure 2A:
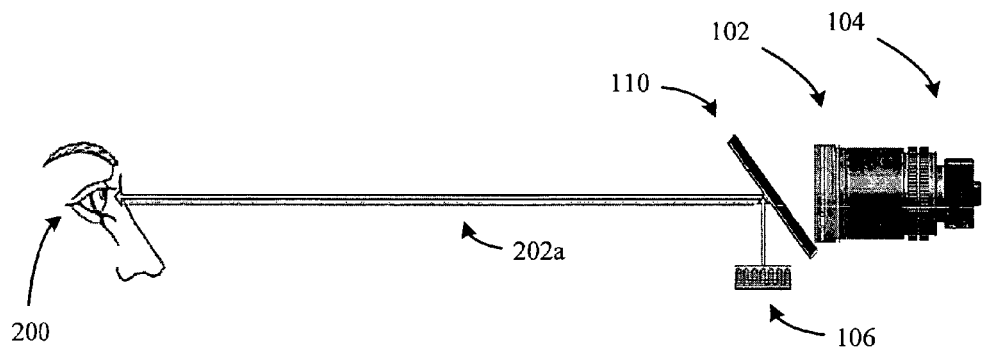
FIGS. 2A and 2B illustrate an LED array with respect to the limiting aperture of a lens component coupled to an image capture component of the photorefraction ocular screening device, in accordance with embodiments of the present invention.
Figure 2B:
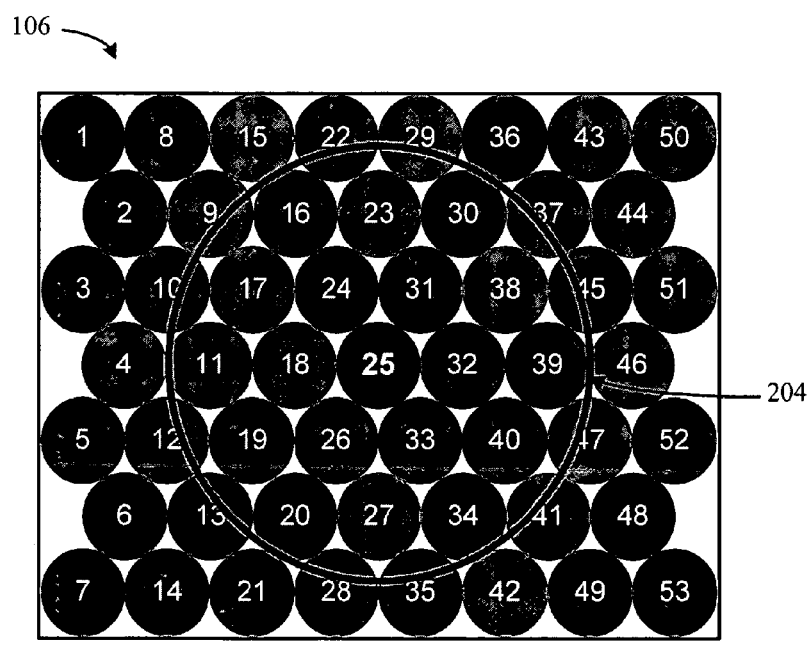

NIR LED stimuli preferably have a center wavelength of 850 nanometers and are directed at an examinee for purposes of capturing images of the pupil for conducting an ocular examination. In one embodiment, referring to FIGS. 2A and 2B, LED array 106 may be comprised of fifty-three (53) NIR LEDs 106b arranged in a hexagonal configuration around a center NIR LED 25, which is positioned so as to be aligned with the optical axis of lens component 102 coupled to image capture component 104 of device 100. When light is emitted from NIR LEDs 106b, it is reflected off beam splitter 110 and transmitted in a direction 202a towards an examinee's eyes 200. Use of beam splitter 110 in device 100 permits light emitted from NIR LEDs 106b to be directed along the optical axis without obscuring lens component 102. In an alternate embodiment, it is envisioned that an arrangement of visible LEDs may also be used in place of NIR LEDs 106b for conducting an ocular examination.

The arrangement of NIR LEDs 106b in LED array 106 allows for flexibility in the illumination patterns that may be presented to examinee's eyes 200. Using NIR LEDs 106b arranged in LED array 106, three types of illumination are available. The illumination types may include an on-axis (coaxial) illumination from center NIR LED 25, an off-axis (decentered) illumination from any one of NIR LEDs 106b (excluding center NIR LED 25) arranged within a limiting aperture space 204 associated with lens component 102, and an off-axis (decentered) illumination from any one of NIR LEDs 106b arranged outside limiting aperture space 204. NIR LEDs 106b may be characterized in terms of their decentration from the center optical axis (zero being at central NIR LED 25) and their angle in a plane perpendicular to the optical axis. For example, referring to LED array 106 illustrated in FIG. 2B, NIR LED 31 is an LED arranged within limiting aperture space 204. NIR LED 31 is identified as having a decentration distance of 6.35 mm from the optical axis, which is aligned with central NIR LED 25, with an angle of 60° from the horizontal axis.

The ocular response of an eye for any given refractive error will depend on the illumination pattern selected. For example, less decentered LEDs offer better resolution for small refractive errors, while more decentered LEDs extend the range of refractive error that can be detected. By comparing the response of an examinee's eyes under different illumination patterns, as described herein, ambiguities commonly associated with refractive error determinations in classical photorefraction may be addressed.

Figure 3A:
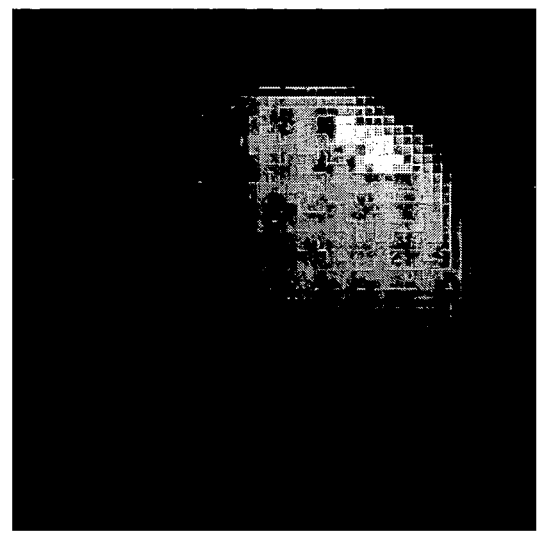
FIGS. 3A and 3B illustrate a comparison of reflexes at the pupil plane, respectively, from eccentric illumination alone and decentered plus coaxial illumination, in accordance with embodiments of the present invention.
Figure 3B:
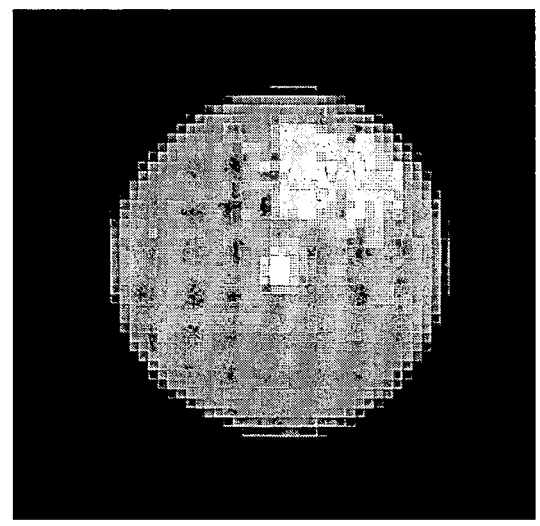

By integrating the use of decentered LEDs within aperture space 204, a broader range of ocular responses are made available. Additionally, with the use of center NIR LED 25, yet a further dimension is enabled, which provides for a co-axial photorefraction response. An exemplary comparison of reflexes associated with different approaches for illuminating a pupil is illustrated in FIGS. 3A and 3B. In FIG. 3A, the crescent reflex produced from an eccentric illumination alone is shown. In FIG. 3B, a reflex produced from a decentered illumination (i.e., one of NIR LEDs 106b) paired with a coaxial (i.e., NIR LED 25) illumination is shown. As can be seen from a comparison of FIGS. 3A and 3B, the boundary of the depicted pupil is more discernible in the latter approach using a coaxial illumination together with a decentered illumination. The two illumination signals are additive, thereby producing a well-illuminated pupil having easily detectable pupil boundaries.

In the illumination arrangements described herein, all stimuli presented to an examinee consist of coaxial center NIR LED 25 combined with any one of decentered NIR LEDs 106b, decentered NIR LEDs 106b being selected at varying decentration distances from the center optical axis lying within and outside of limiting aperture space 204. In addition to using paired stimuli, the illumination arrangements described herein also comprises presenting a stimulus to an examinee consisting of only coaxial center NIR LED 25. Using center NIR LED 25 in all stimuli illumination arrangements ensures that the pupil is always sufficiently illuminated, allowing it to be acquired and measured reliably. Unlike other known implementations of photorefraction, providing a decentered illumination paired with a coaxial illumination, using the LED irradiation sources in LED array 106, does not result in a reflex having crescents, thereby allowing a crescent's geometry to be omitted from the process for determining refractive error.

When illuminating a pupil for purposes of conducting an ocular examination, specific stimuli need to be selected to ensure good pupil imaging and accurate determination of refractive error. Additionally, the specific stimuli selected must serve to allow for determination of asymmetry (astigmatism or cylinder refractive error) in an eye's refractive power. The foregoing criteria are met through the use of decentered and coaxial LED pairing, wherein illumination patterns selected to serve as stimuli are dependent not only on the distance of NIR LEDs 106b from the center optical axis of lens component 102, but also their orientation with respect to the axis of an examinee's cylinder axis.

Figure 4A:
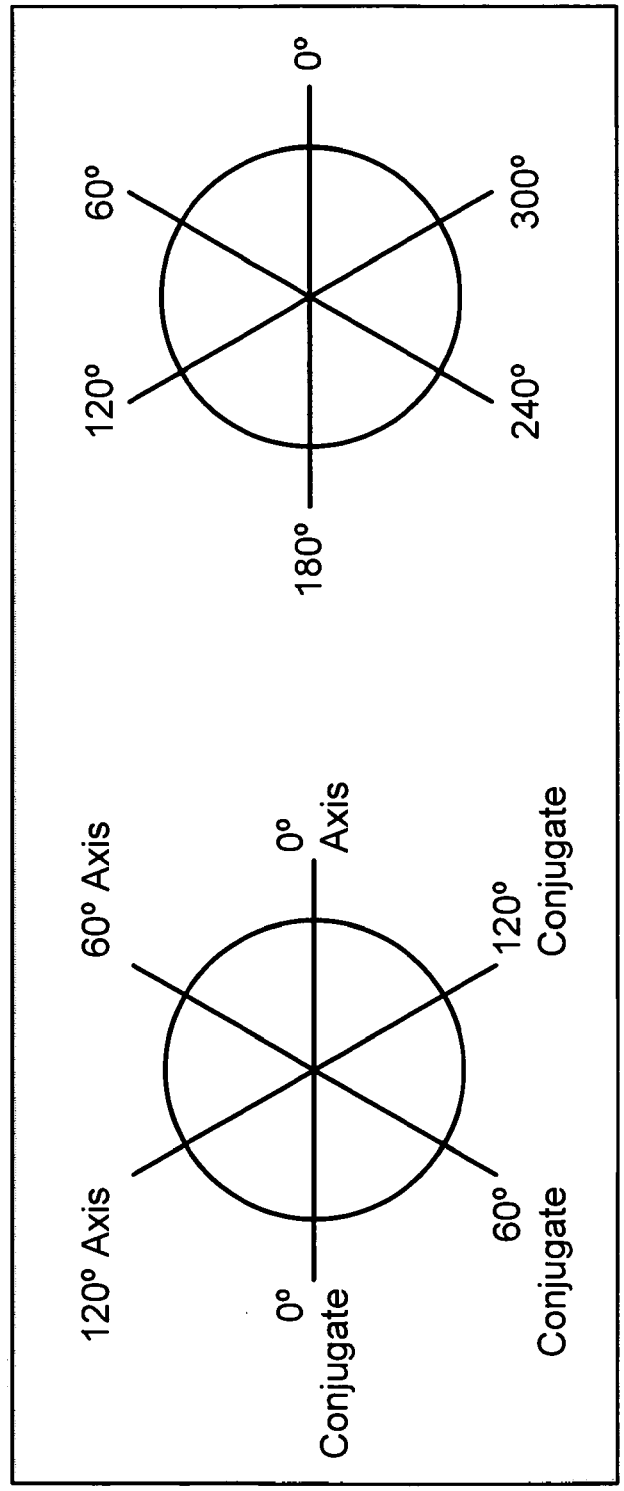
FIG. 4A illustrates three primary axis-conjugate meridians, and FIGS. 4B-4D provide tables illustrating paired LED stimuli that may selected in one of the three primary meridians at varying degrees of decentrations, in accordance with embodiments of the present invention.

Decentricity pairing is illustrated in the charts of FIGS. 4B-4D using the three primary axis-conjugate meridians illustrated in FIG. 4A. A reference made herein to an axis line is the angle of a line, in the plane of LED array 106, extending outward from central NIR LED 25. A reference made herein to a conjugate line (also called the "explementary") is the angle of a line, in the plane of LED array 106, defined by either adding or subtracting 180° to the angle corresponding to the axis line. Thus, for example, the conjugate line of a 120° axis line is 300°. An extended line comprising both of the lines defining the axis line and its conjugate line, as illustrated in FIG. 4A, is referred to collectively as the meridian and is identified herein by the angle corresponding to the axis line, which is less than or equal to 180°. Thus, for example, the combination of the 120° axis line and its 300° conjugate line is identified as the 120° meridian.

The start of image data collection is carried out using decentricity pairings along the three primary axis-conjugate meridians illustrated in FIG. 4A. Paired stimuli may be selected at three decentration positions extending along the axis line and at three decentration positions extending along the corresponding conjugate line of a selected meridian. Decentricity pairings for the 0° meridian are illustrated in the chart of FIG. 4B. In the 0° meridian, center NIR LED 25 is paired with a NIR LED 106b at decentration positions 6.35 mm, 12.70 mm and 19.05 mm along the 0° meridian. Since decentricity pairing is performed for the 0° meridian in both the axis line and its corresponding conjugate line, a total of six different decentricity pairings are provided for the 0° meridian. For example, as illustrated in the chart of FIG. 4B, a decentration position of 6.35 mm along the axis line in the 0° meridian utilizes paired stimuli comprised of center NIR LED 25 and a decentered NIR LED 32, while the same decentration position in its corresponding conjugate line is comprised of center NIR LED 25 and a decentered NIR LED 18.

Since decentricity pairing is also repeated for the 60° and 120° meridians, as illustrated respectively in the charts of FIGS. 4C and 4D, six different decentrations are obtained for each of those meridians as well. For example, as illustrated in the chart of FIG. 4C, a decentration position of 6.35 mm along the axis line in the 60° meridian utilizes paired stimuli comprised of center NIR LED 25 and a decentered NIR LED 31, while the same decentration position in its corresponding conjugate line is comprised of center NIR LED 25 and a decentered NIR LED 26. Similarly, as illustrated in the chart of FIG. 4D, a decentration position of 6.35 mm along the axis line in the 120° meridian utilizes paired stimuli comprised of center NIR LED 25 and a decentered NIR LED 24, while the same decentration position in its corresponding conjugate line is comprised of center NIR LED 25 and a decentered NIR LED 33. Collectively, a total of eighteen (18) ocular responses may be obtained through the use of decentricity pairings in the three primary axis-conjugate meridians (six decentricity pairings for each of the 0°, 60° and 120° meridians).

Figure 5A:
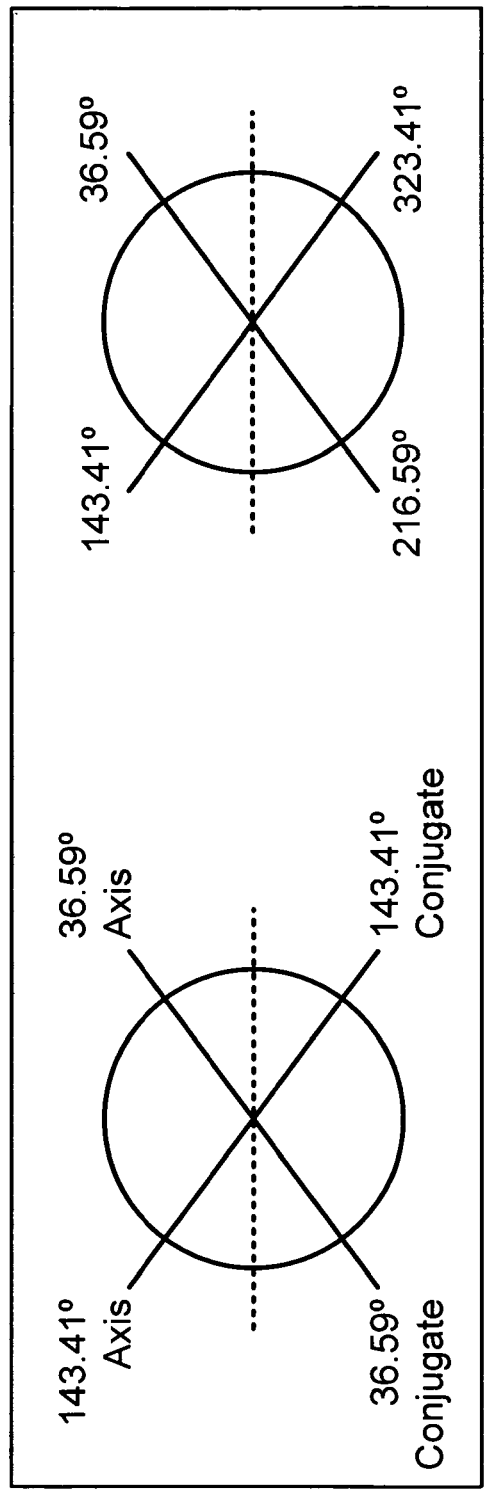
FIG. 5A illustrates two supplementary meridians, and FIG. 5B provides a table illustrating paired LED stimuli that may be selected in one of the two supplementary meridians at varying degrees of decentrations, in accordance with embodiments of the present invention.

In addition to the decentered stimuli in the three primary axis-conjugate meridians, decentered stimuli at the far corners of LED array 106 may also be utilized. The angles defining the axis and corresponding conjugate lines associated with these decentered stimuli are referred to herein as the supplementary meridians. Decentricity pairing of stimuli in the supplementary meridians may be used to disambiguate the interpretation of ocular reflexes obtained in the three primary axis-conjugate meridians. The supplementary meridians are defined along the axis-conjugate of 36.59°-216.59° and 143.41°-323.41°, as illustrated in FIG. 5A, and are referred to herein, respectively, as the 36.59° and the 143.41° meridians.

As in the three primary meridians, paired stimuli in the supplementary meridians are identified by a decentration position along the axis line and the corresponding conjugate line for each of the 36.59° and the 143.41° meridians. Decentricity pairings for the 36.59° and the 143.41° meridians are illustrated in the chart of FIG. 5B. In the 36.59° meridian, center NIR LED 25 is paired with a NIR LED 106b at a decentration position 27.68 mm from center NIR LED 25. Since decentricity pairing is performed in both the axis line and its corresponding conjugate line, a total of two different decentricity pairings are provided for the 36.59° meridian. For example, as illustrated in FIG. 5B, a 27.68 mm decentration position in the axis line of the 36.59° meridian utilizes paired stimuli comprised of center NIR LED 25 and a decentered NIR LED 50, while its corresponding conjugate line is comprised of center NIR LED 25 and a decentered NIR LED 7. A similar decentricity pairing, in the axis and its corresponding conjugate lines, is performed for the 143.41° meridian. The decentricity pairing of stimuli in the supplementary meridians provide for an additional four (4) stimuli to the eighteen (18) stimuli provided by the three primary meridians, thereby providing for a total of twenty-two (22) ocular responses that may be used in determining refractive error for an examinee.

Figure 6:
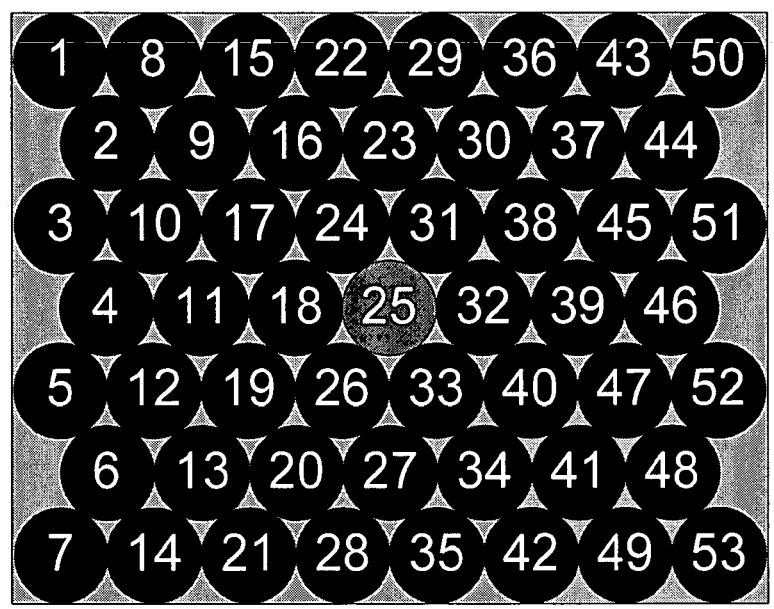
FIG. 6 illustrates selection of a co-axial LED stimulus without pairing to a decentered LED stimulus, in accordance with embodiments of the present invention.

In addition to the use of paired stimuli in the three primary meridians and the two supplementary meridians, a single coaxial stimulus may also be utilized to obtain an ocular response. The co-axial stimulus is center NIR LED 25, as illustrated in FIG. 6. The purpose of this stimulus is to ensure that there are no issues pertaining to reflectivity of an eye and that the illumination provided by device 100 is functioning according to specifications. With the decentricity pairing of stimuli in the three primary meridians, the decentricity pairing of stimuli in the two supplementary meridians and the single coaxial stimulus, a total of twenty-three (23) ocular responses may be captured for use in determining refractive error of an examinee. The presentation of these 23 stimuli, and the collection of corresponding pupil images captured in response to each, is referred to as the examination protocol, which is further described herein with reference to process 860 of FIG. 8D.

Image Capture & Pupil Acquisition

Digital image feature detection and filtering is used for pupil acquisition in images captured by image capture component 104. The implementation of digital image feature detection and filtering may be dependent on the sensor resolution of image capture component 104, the distance of an examinee's pupil from image capture component 104, and the field of view determined by the optics of lens component 102 coupled to image capture component 104. Basic physiological constants (e.g., average pupil size) may also enter into the filtering process, along with acceptable pupil diameter maxima and minima.

Figure 7A:
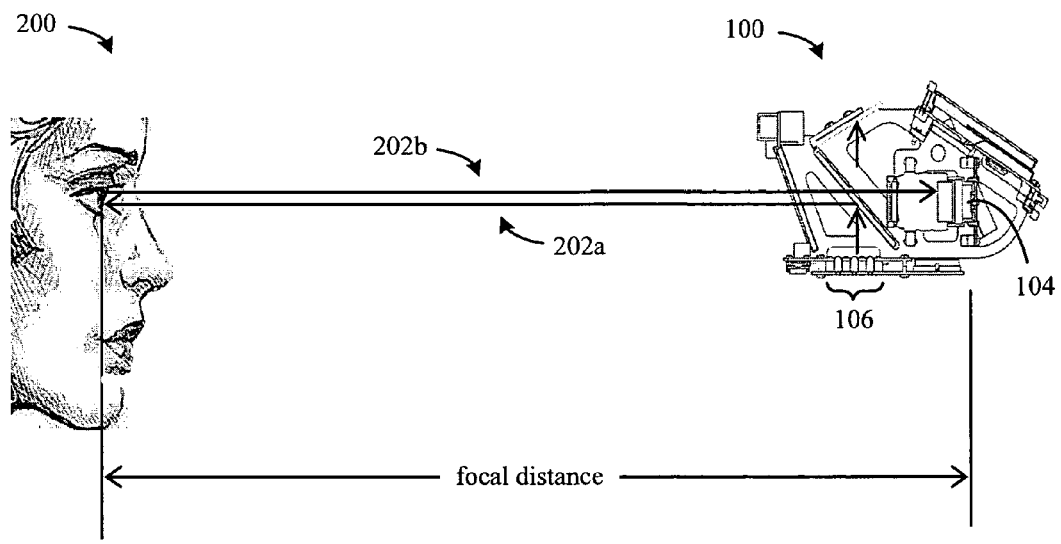
FIG. 7A illustrates emitted and refracted light paths between an examinee and the photorefraction ocular screening device.

An exemplary distance relationship between device 100 and the examinee is illustrated in FIG. 7A, where lens component 102 is selected and adjusted to have an optimal focus at a focal distance from examinee's eyes 200. The focal distance between device 100 and the examinee's eyes 200 may be changed without affecting the image capture process if sensor resolution of image capture component 104, field of view and calibration of refractive errors are all adjusted accordingly. As illustrated in FIG. 7A, light emitted from LED array 106 is reflected and transmitted in a direction 202a along the optical axis towards examinee's eyes 200. Light reflected back and exiting examinee's eyes 200 is returned in a direction 202b and received at image capture component 104 of device 100.

Figure 7B:
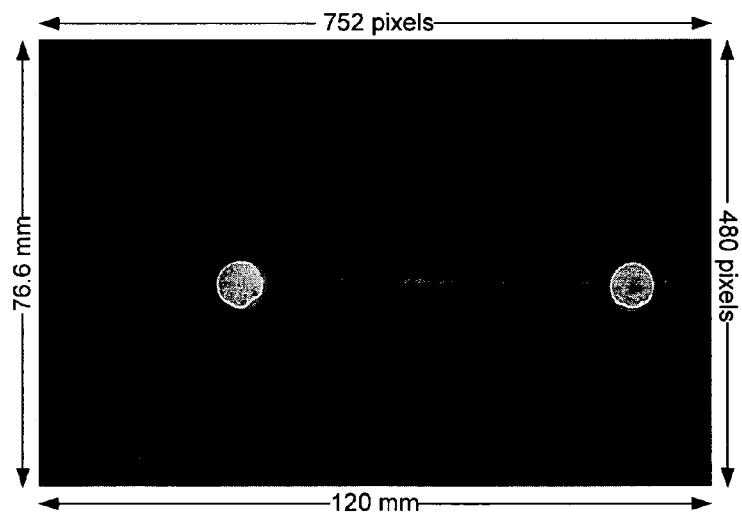
FIG. 7B illustrates full-frame dimensions of an image capture received at the photorefraction ocular screening device, in accordance with embodiments of the present invention.

Using one (1) meter as the focal distance between device 100 and examinee's eyes 200, sensor resolution of image capture component 104 may be set at 752 (horizontal) by 480 (vertical) pixels, as illustrated in FIG. 7B. At a distance of 1 meter, a 120 mm (horizontal) by 76.6 mm (vertical) field of view may be provided by image capture component 104 given a selected lens component 102. With these measurements, a conversion factor of 6.267 pixels/mm may be established. The established conversion factor may be used as a calibration constant to formulate parameters needed for digital filtering. It should be noted that this is merely an exemplary embodiment and alternate embodiments are envisioned, wherein a different lens or sensor is used or the focal distance is adjusted, but where the operating principle of the present invention remains the same.

Figure 8A:
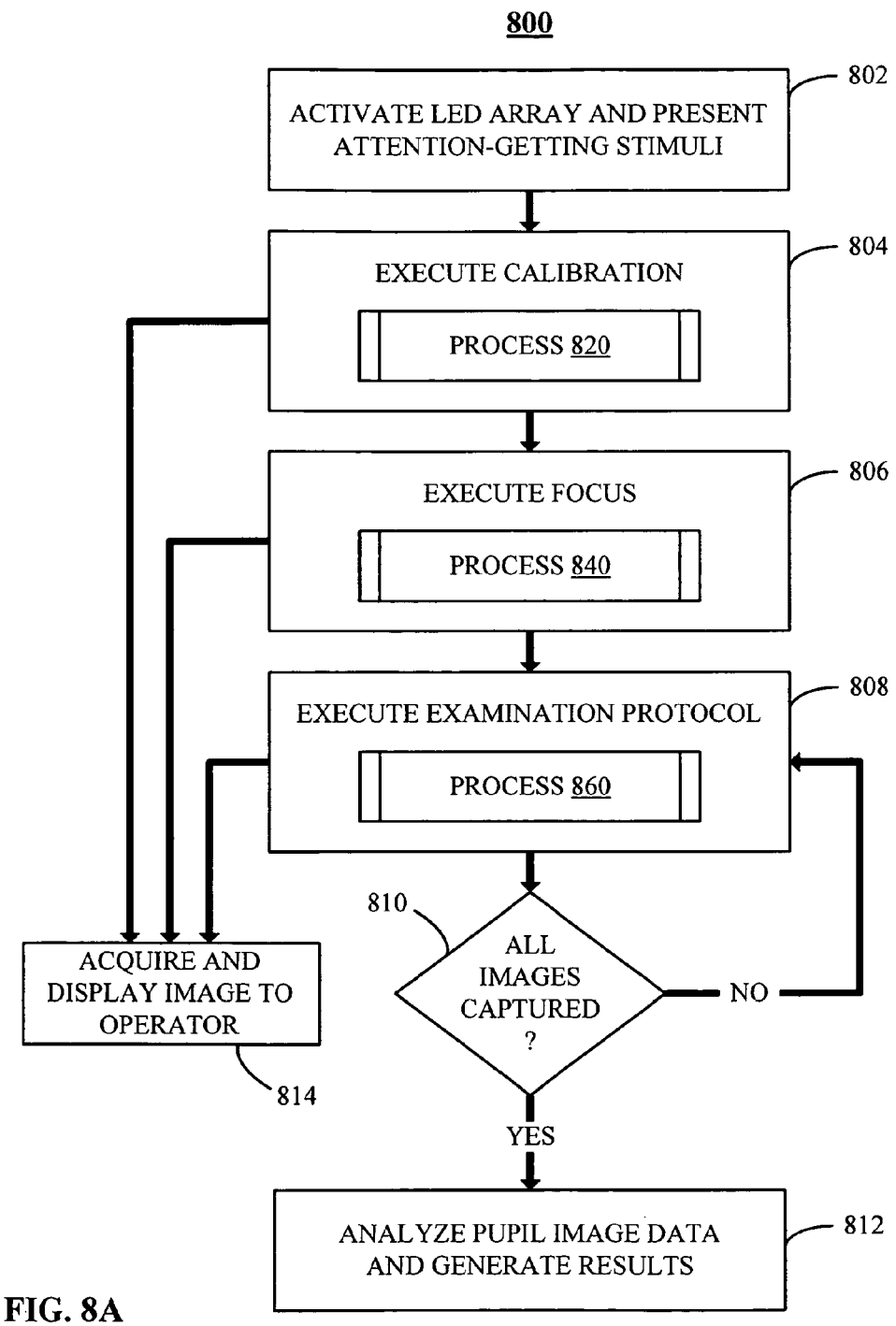
FIG. 8A is a flowchart illustrating a general overview of an image acquisition and analysis process engaged in by the photorefraction ocular screening device during an ocular examination, and corresponding

FIG. 8A illustrates a flowchart providing a general overview of an image data acquisition and analysis process 800 executed by processing logic under computer program control in device 100. Process 800 may be initiated upon activation of LED array 106, at step 802, and presentation of attention-getting stimuli to an examinee. Images captured in response to visual stimuli presented to the examinee are processed along two separate paths in process 800, a first path providing an operator display image and a second path providing clinically relevant information for analysis of captured images.

In providing a display image, a copy of raw data received at image capture component 104 may be contrast enhanced and transformed into a standard display format for presentation and feedback to an operator of device 100. For example, the display image may be presented on operator display screen 114 of device 100. The image provided on operator display screen 114 may be overlaid with information such as, for example, an examinee's distance from device 100, quality of focus, progress of the examination, other operator-relevant information or combinations thereof.

There are three distinct phases in process 800 associated with the path intended to provide clinically relevant information. More specifically, processing logic under computer program control in device 100 may execute at steps 804, 806 and 808, a calibration phase, a focus phase and an examination protocol phase, respectively, to acquire pupil image data for refractive error analysis. Raw image data acquired at each of these phases may be made available for display to an operator, at step 814, on operator display screen 114 of device 100.

The intensity of a reflex from a pupil can vary widely among examinees due mainly to refractive error and pupil size. Since the dynamic range of the sensor in image capture component 104 is limited, an optimal exposure time must be found to insure that the reflex of an examinee is both detectable and not saturated. To accomplish this, a calibration process 820 is provided using a range of exposure times (e.g., 6, 12 and 18 milliseconds), which may be selected to sample the range of empirically-derived usable exposure times given a selected lens, sensor and LED illumination. Calibration process 820 may be executed, at step 804, to enable the calibration phase of process 800. The steps comprising calibration process 820 are described with reference to the flowchart illustrated in FIG. 8B.

Figure 8B:
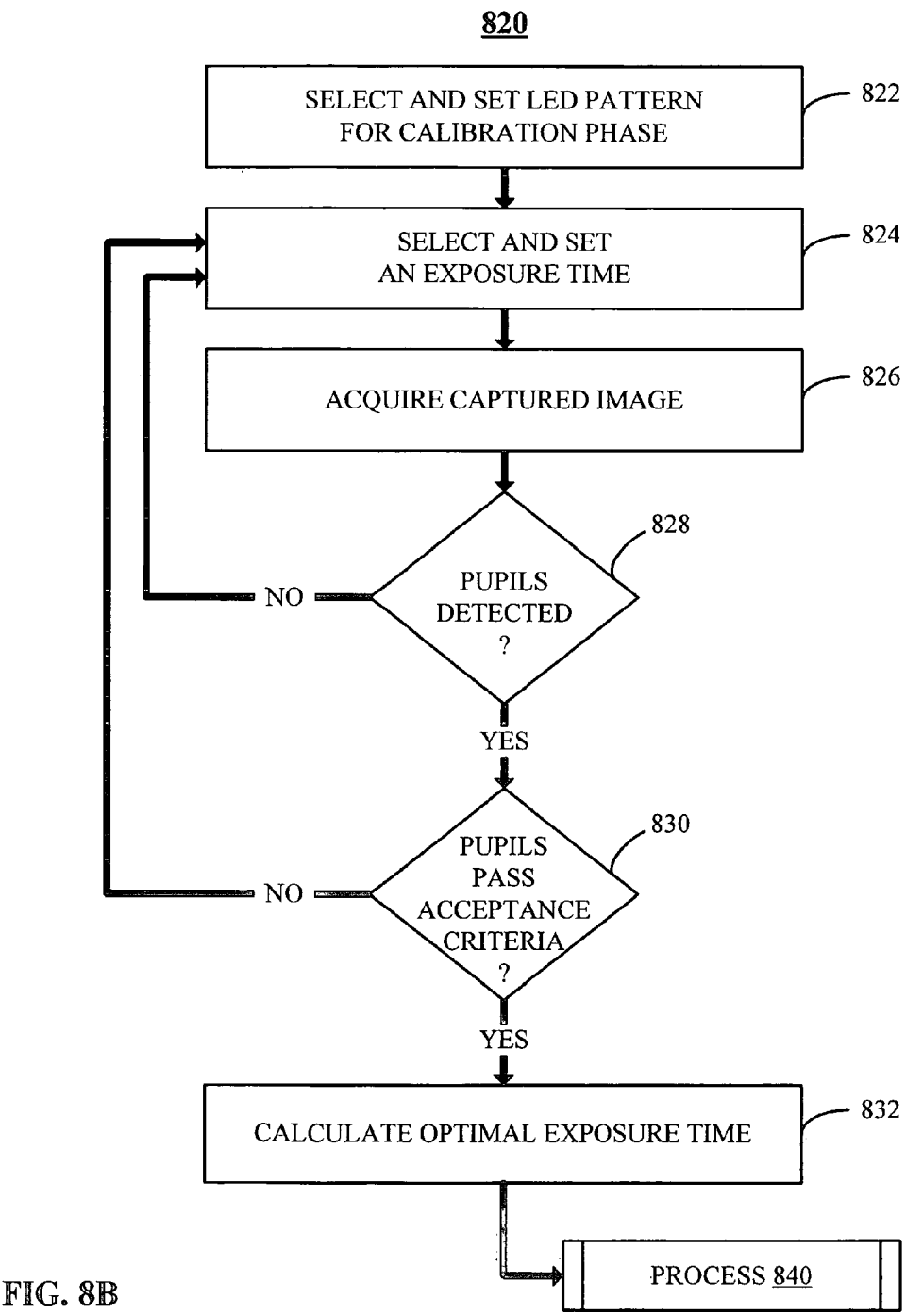
FIGS. 8B-8D are flowcharts illustrating sub-processes associated with three phases executed during image acquisition in the process of FIG. 8A, in accordance with embodiments of the present invention.

Referring to FIG. 8B, calibration process 820 may be initiated by selecting and setting, at step 822, an LED pattern suited for the calibration phase. In a preferred embodiment, NIR LEDs 18, 25 and 32 may be illuminated in order to provide more light than would be delivered by any decentricity pairing stimulus. This insures that a properly calibrated exposure time will not saturate the sensor when a select decentricity pairing stimulus is delivered. After the LED pattern is set, an exposure times may be selected and set, at step 824, for testing. Using the selected exposure time, a captured image may be acquired, at step 826, and a determination may be made, at step 828, whether pupils are detected in the captured image. If pupils are not detected in the captured image, then process 820 may return to selecting and setting, at step 824, a different exposure time. Using the newly selected exposure time, a captured image is again acquired, at step 826, and a determination may be made, at step 828, whether pupils are detected in the captured image. If pupils are detected, the viability of the selected exposure time is further tested by undergoing a second determination, at step 830, to assess whether the pupils pass predetermined acceptance criteria.

Various acceptance criteria may be used for the second determination, at step 830, to assess the suitability of detected pupil images for use in determining an optimum exposure time. These include, but are not limited to, a suitable presence of pupils necessary to perform calibration, an acceptable pupil size having a measurable diameter ranging between 1.5 to 10 mm, an acceptable inter-pupil distance between pupil centers, an acceptable examinee distance from device 100, an acceptable pupil saturation level or combinations thereof.

If a determination is made, at step 830, that detected pupils fail to satisfy one or more predefined acceptance criteria, then process 820 may again return to selecting and setting, at step 824, another exposure time for testing. Process 820 may be repeated to ascertain which of the exposure times provides optimal results—i.e., pupils detected without saturation. Saturation may be defined as greater than 10% of the pixels in the pupil have an intensity value greater than 98% of the maximum value associated with the sensor in image capture component 104. When the pupil image desired is detected, the optimal exposure time may be calculated, at step 832.

The optimum sensor exposure time may be set to 75% of the full sensor range. Once pupils are found, a central 25×11 pixel strip is measured for brightness. The brightness measure is taken to be the mean pupil intensity in this strip. Given the mean intensity value, the optimum exposure time is calculated as follows:

$$ExpTm_{Optimum} = \frac{767.25 * ExpTm_{Current}}{MeanPupilIntensity}$$

When both pupils are included in an examination, the pupil with the brightest mean intensity value may be used in the calculation.

After an optimal exposure time has been calculated, a focus process 840 may be executed, at step 806, to enable the focus phase of process 800. Good focus of the pupil image is necessary for accurately capturing the pupil images. In particular, if the glint from the corneal surface is not well-focused, its position cannot be accurately ascertained and gaze direction may not be measurable. Furthermore, if the glint image is very diffuse and overlaps significantly with the reflex, this will likely result in a poor estimate of refractive error. The steps comprising focus process 840 are described with reference to the flowchart illustrated in FIG. 8C.

Figure 8C:
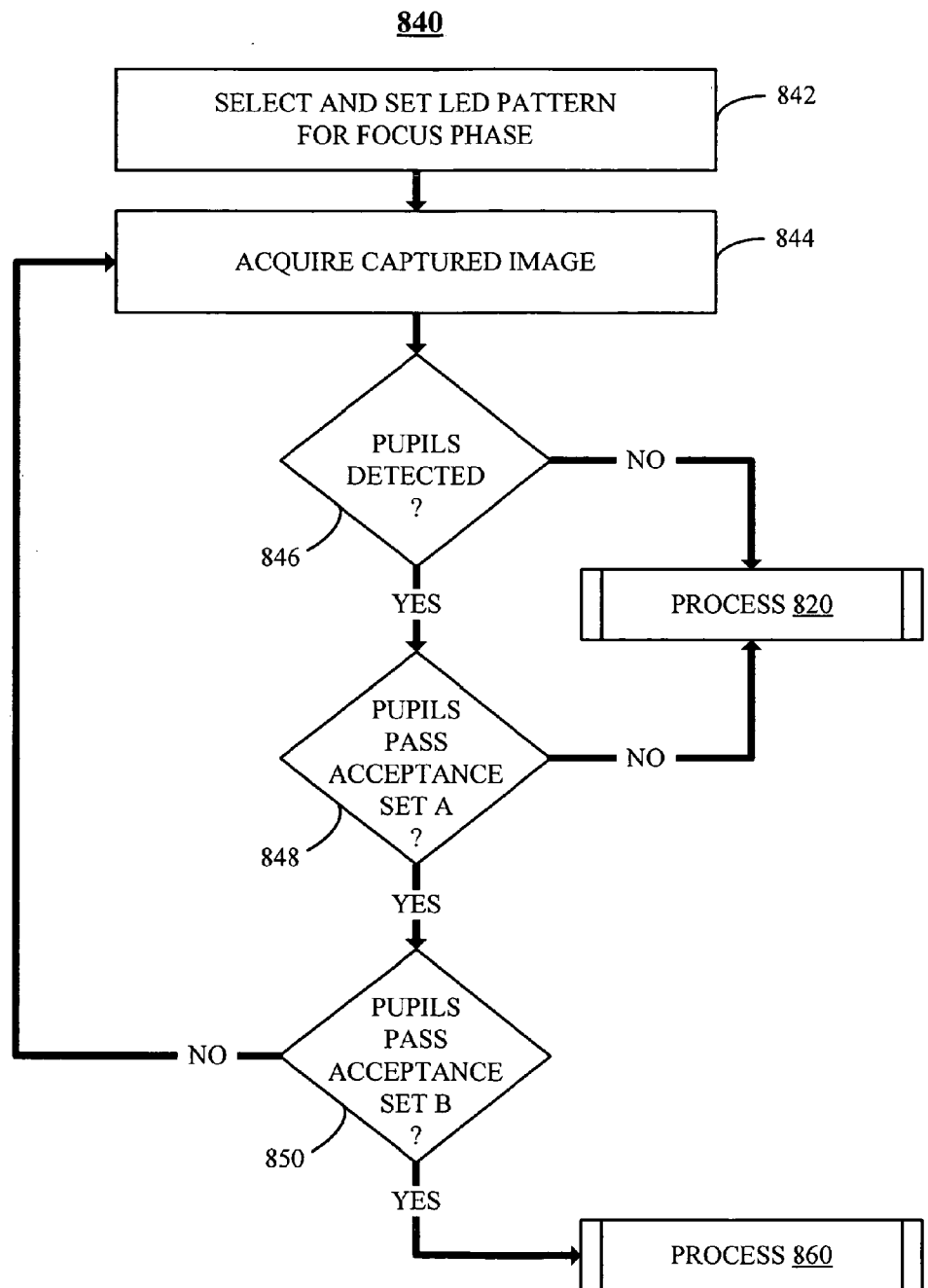

Similar to the calibration phase described in process 820, the focus phase in process 840 assesses the suitability of captured images. Referring to FIG. 8C, focus process 840 is initiated by selecting and setting, at step 842, an LED pattern suited for the focus phase. In a preferred embodiment, NIR LEDs 18, 25 and 32 may be illuminated in order to ensure sufficient reflected light is returned through the pupil. After the LED pattern is set, a captured image may be acquired, at step 844, and a determination may be made, at step 846, whether pupils are detected in the captured image. If pupils are not detected in the captured image, then process 840 may revert back to process 820 to reinitiate the calibration phase. If pupils are detected, the pupil images may then be subject to supplemental determinations, at steps 848 and 850, to assess whether the pupils pass a first set and a second set, respectively, of acceptance criteria.

The first set of acceptance criteria utilized in process 840 may be similar to the acceptance criteria utilized in process 820—i.e., suitable presence of pupils, acceptable pupil size and acceptable inter-pupil distance. If a determination is made, at step 848, that detected pupils fail to satisfy the first set of acceptance criteria, then process 840 may again revert back to process 820 to reinitiate the calibration phase. If the detected pupils satisfy the first set of acceptance criteria, then the detected pupil may then be tested, at step 850, against the second set of acceptance criteria. The second set of acceptance criteria is used to assess the glint and gaze direction. If a determination is made, at step 850, that the pupil images do not yield the presence of the glint or an acceptable gaze direction, then process 840 may acquire, at step 842, a new captured image.

When the determination, at step 850, concludes that the second set of acceptance criteria is satisfied, the calibration and focus phases are complete and process 800 may then proceed with executing, at step 808, examination protocol process 860. In process 860, the criteria for determining image suitability are stricter than in the calibration and focus phases associated, respectively, with process 820 and process 840. In addition to standard image measures, changes in some images measures may be performed to reduce the possibility of blur in the images. Changes in image measures are preferably performed between a current image and a reference image, which is typically the image preceding the current image. The steps comprising examination protocol process 860 are described with reference to the flowchart illustrated in FIG. 8D.

Figure 8D:
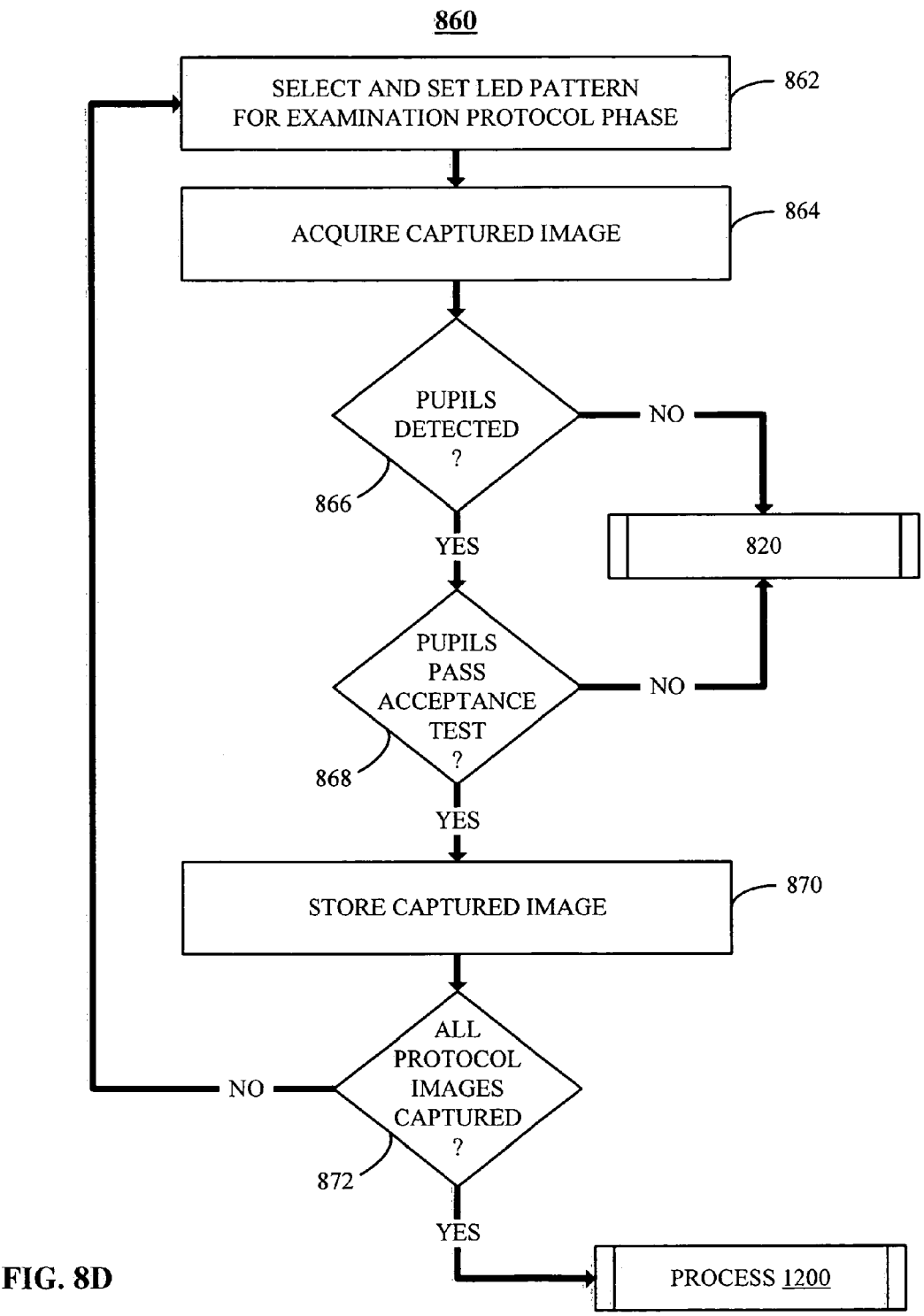

Referring to FIG. 8D, examination protocol process 860 is initiated by selecting and setting, at step 862, one of the 23 stimuli LED patterns. Using the selected LED pattern, the corresponding captured image is acquired, at step 864. Upon acquiring the captured image, an initial determination is made, at step 866, to verify again that pupils have been detected in the captured image. If pupils are not detected in the captured image, then process 860 may revert back to process 820 to reinitiate the calibration phase. If pupils are detected, the pupil images are then subject to a second determination, at step 868, to assess whether the detected pupils pass acceptance criteria, as previously described in process 840 used for establishing focus. As in process 840, if one or more acceptance criteria in process 860 are determined to be noncompliant, process 860 may revert back to the calibration phase of process 820.

In a preferred embodiment, depending on the criteria failure detected, process 860 may determine whether it is necessary to return to the calibration phase of process 820 or only the focus phase of process 840. Criteria failures resulting in a return to the calibration phase of process 820 may include, but are not limited to, absence of pupils in the current image, unacceptable pupil size(s) in either the current or reference images, unacceptable change in pupil size between current and reference images, unacceptable inter-pupil distance in the current image, unacceptable change in the inter-pupil distance between current and reference images, or unacceptable gaze direction in either the current and reference images. Criteria failures resulting in a return only to the focus phase of process 840 may include, but are not limited to, absence of pupils in the reference image, unacceptable change in pupil position between current and reference images, unacceptable inter-pupil distance in the reference image, unacceptable glint position(s) in either the current and reference images, unacceptable change in glint position(s) between current and reference images, or unacceptable change in gaze direction between current and reference images.

When criteria associated with the determination, at step 868, are satisfied, the acquired image may be stored, at step 870, to be used in the refractive error analysis. After the acquired image is stored, at step 870, an additional determination may be made, at step 872, to identify whether images associated with any of the 23 stimuli LED patterns remain to be captured. Process 860 may be repeated until each of the 23 stimuli LED patterns, and the corresponding acquired image for each, satisfies acceptance criteria and is stored. Once all of the 23 images are acquired and stored, process 800 may then proceed with executing, at step 812, an analysis of the ocular responses associated with each of the saved images for purposes of conducting the refractive error and gaze analyses.

Figure 9:
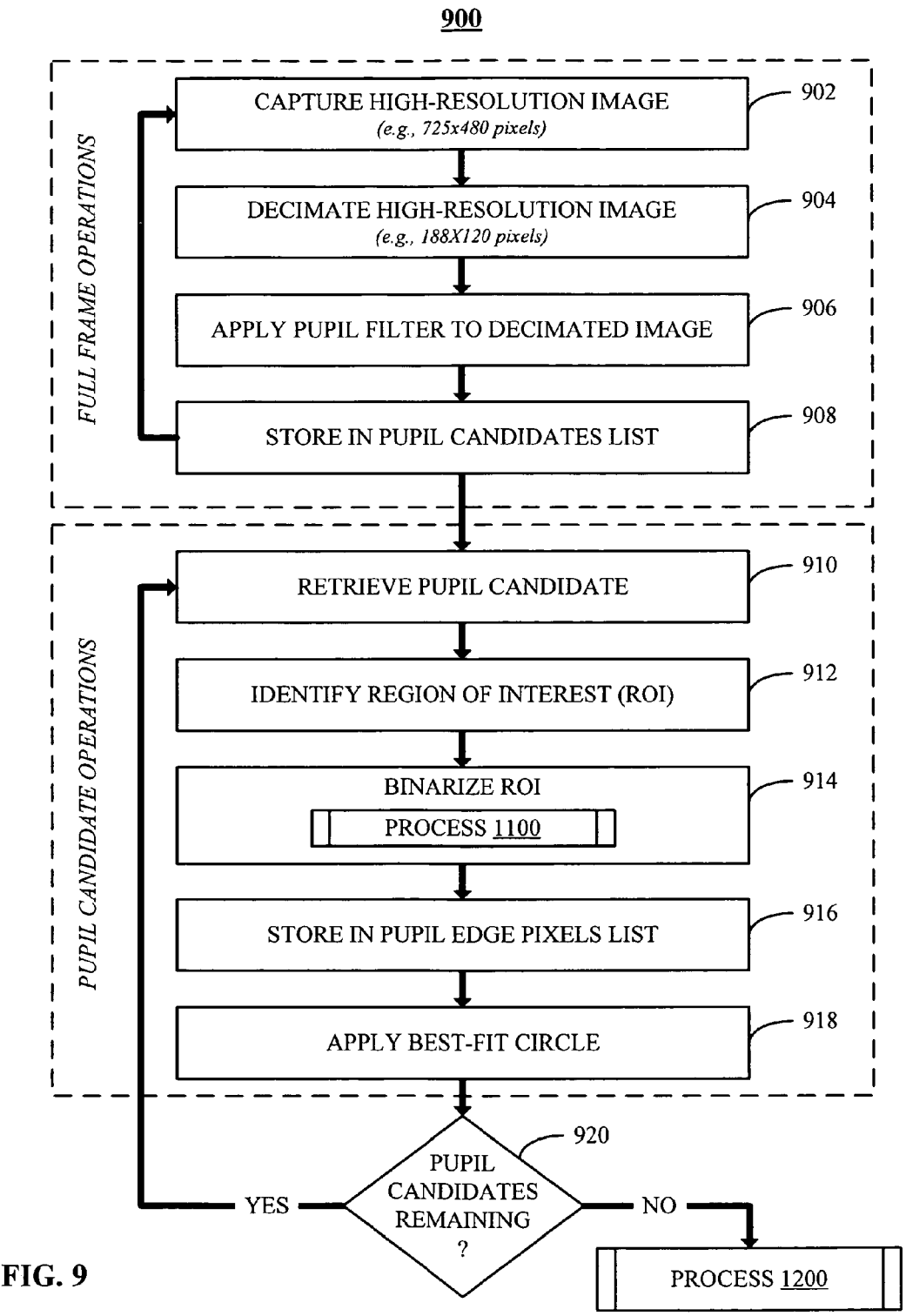
FIG. 9 is a flowchart illustrating a process engaged by the photorefraction ocular screening device associated with pupil acquisition, distinguishing full frame operations and pupil candidate operations, in accordance with embodiments of the present invention.

Acquisition of pupil images occurs throughout an ocular examination until all images associated with the examination protocol phase (i.e., presentation of the 23 stimuli and collection of corresponding ocular responses) are successfully captured. As such, a reliable method for detecting pupils must be employed. The method employed by device 100 is described with reference to the flowchart illustrated in FIG. 9, which depicts a highly reliable pupil acquisition process 900.

Pupil acquisition process 900 may be comprised of two basic operations, full frame operations (steps 902-908) and pupil candidate operations (steps 910-918). To initiate pupil acquisition process 900, a high resolution image is captured, at step 902, by image capture component 104 upon presenting near-infrared stimuli to an examinee. As previously described, image capture component 104 may be set at 752 (horizontal) by 480 (vertical) pixels, as illustrated in FIG. 7B, to provide for a high-resolution image capture. Upon acquiring the high-resolution image capture, the image may be decimated, or sub-sampled, at step 904, to reduce computation time for preliminary isolation of pupil candidates. For example, in decimating the high-resolution image, every fourth pixel may be copied into a sub-sampled array, thereby providing an image that is $\frac{1}{16}^{th}$ of the high-resolution image (i.e., 188×120 pixels).

Once the high-resolution image has been decimated, a pupil filter may be applied, at step 906, using a two-pass procedure configured to enhance pixels likely to be located within the pupils. Each pass may apply an optimized kernel, based on a pupil—non-pupil template, scanning for how well surrounding pixels fit the template. Application of the kernel may be optimized for speed by considering only a limited number of symmetrically-spaced surrounding pixels instead of a whole matrix of possible points. An exemplary optimized pupil filtering kernel is illustrated in FIG. 10.

Figure 10:
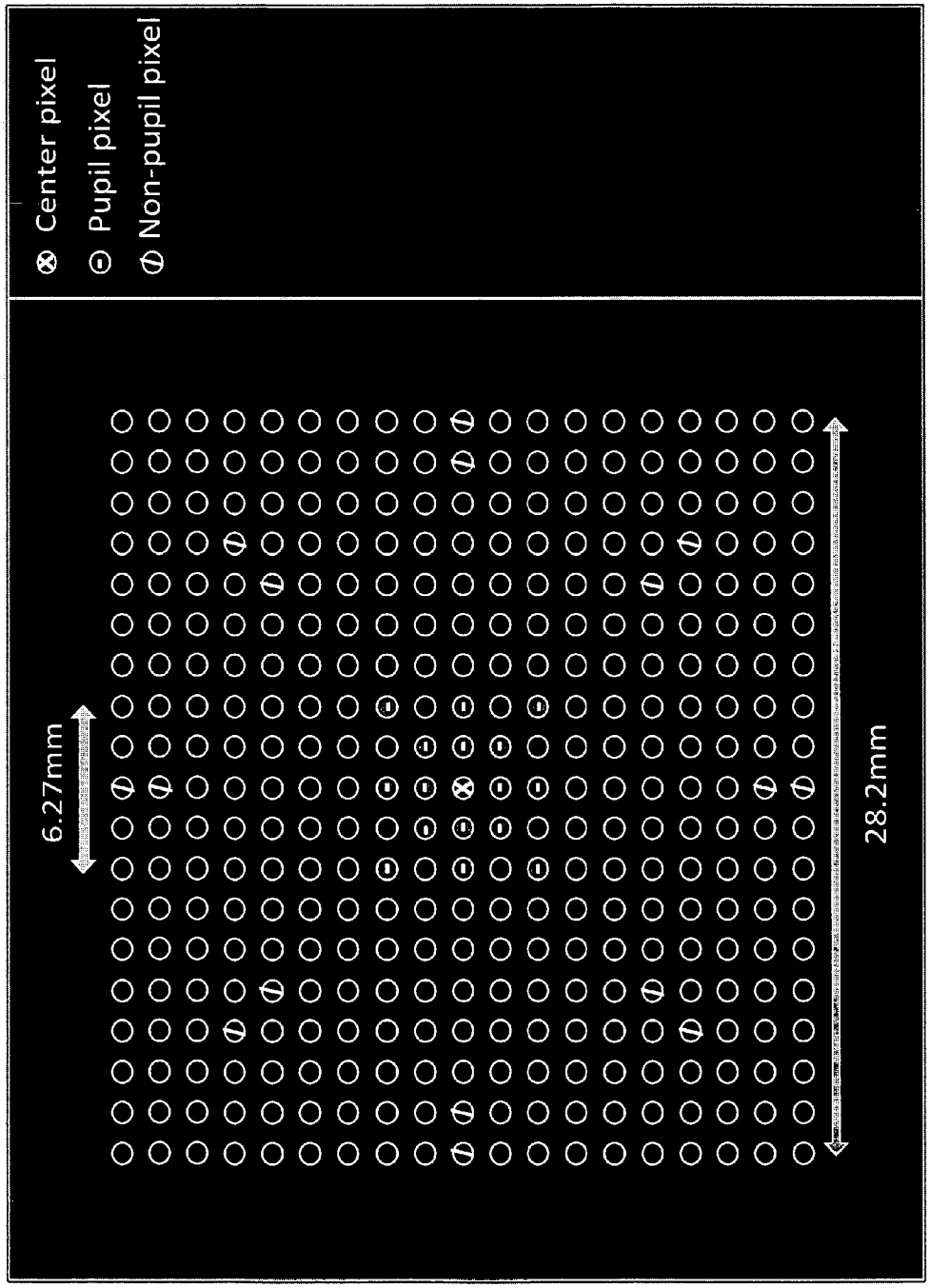
FIG. 10 illustrates an optimized pupil filtering kernel, in accordance with embodiments of the present invention.

Referring to FIG. 10, a pixel designated with a "x" reference mark corresponds to the center pixel of the kernel template, pixels designated with a "-" reference mark are considered to be pixels located in a pupil region of the kernel template, and pixels designated with a "/" reference mark are considered to be pixels located in a non-pupil region of the kernel template. The remaining sections of the kernel template, lying between the designated pupil and non-pupil regions, are neither examined nor used, thereby allowing for varying pupil sizes to be accommodated by the kernel template. All other pixels, unmarked in FIG. 10, are similarly not examined.

Using the pupil filtering kernel template of FIG. 10, maximum output is achieved when pixels in the designated pupil region of the template have a high intensity and pixels in the designated non-pupil region of the template have a low intensity. Initially, the output may be the difference between the average pupil and the average non-pupil pixel intensities. The output may be reduced further when the non-pupil intensity values are similar to the background (average image intensity) and when the variance of the inner and outer non-pupil pixel rings increases.

After application of the pupil filtering kernel, the resulting enhanced image may be saved, at step 908, into a pupil candidate list. A candidate pupil map may be generated using a combined thresholding and pixel connectedness procedure. The threshold may be empirically determined from the filtered output and may be calculated as follows:

$$\text{Threshold} = \text{Mean\_Background} + \left[\frac{\text{Max\_Output} - \text{Mean\_Background}}{6}\right]$$

Where a mean background value is representative of the average pixel intensity of an entire filtered output image and where a max output value is representative of the highest intensity in the filtered output image. Pixel-connectedness may be based on a flood fill algorithm, where connected pixels are assigned a candidate identifier. In many cases, multiple candidates will be present in each candidate map.

Upon completing the full frame operations, a transition may then be made to the pupil candidate operations of process 900. The pupil candidate operations are performed on each image stored, at step 908, in the pupil candidate list. A pupil candidate may be retrieved, at step 910, to initiate the pupil candidate operations. For each pupil candidate retrieved, a bounding rectangle encompassing the pupil candidate is provided. Dimensions defining the sides of the bounding rectangle may be determined by the left-most and right-most pixel column numbers of a pupil candidate, and the top-most and bottom-most pixel rows of the pupil candidate. Pupil candidates having bounding rectangles with a width or height that is comprised of less than two (2) pixels are immediately rejected. If a pupil candidate is retained, the center of the bounding rectangle may be adjusted to match the equivalent position in a corresponding high resolution image of the pupil candidate, generating an initial bounding square (65×65 pixels) for identifying, at step 912, a region of interest (ROI) in the high resolution image. All operations from this point forward may be performed on the high resolution version of the ROI sub-image.

Figure 11A:
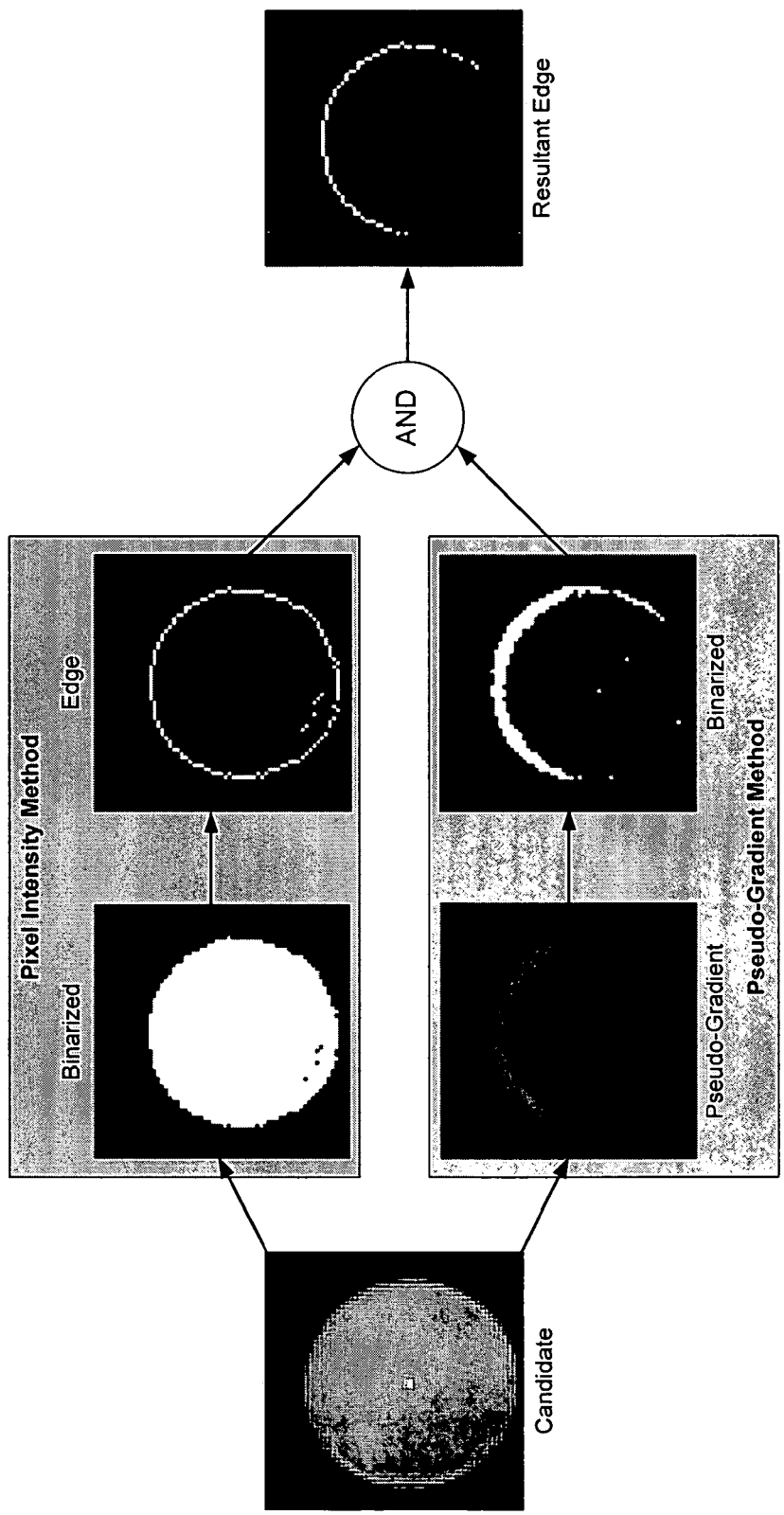
FIG. 11A illustrates a dual-method approach for binarizing a pupil candidate to identify pupil edge pixels.
Figure 11B:
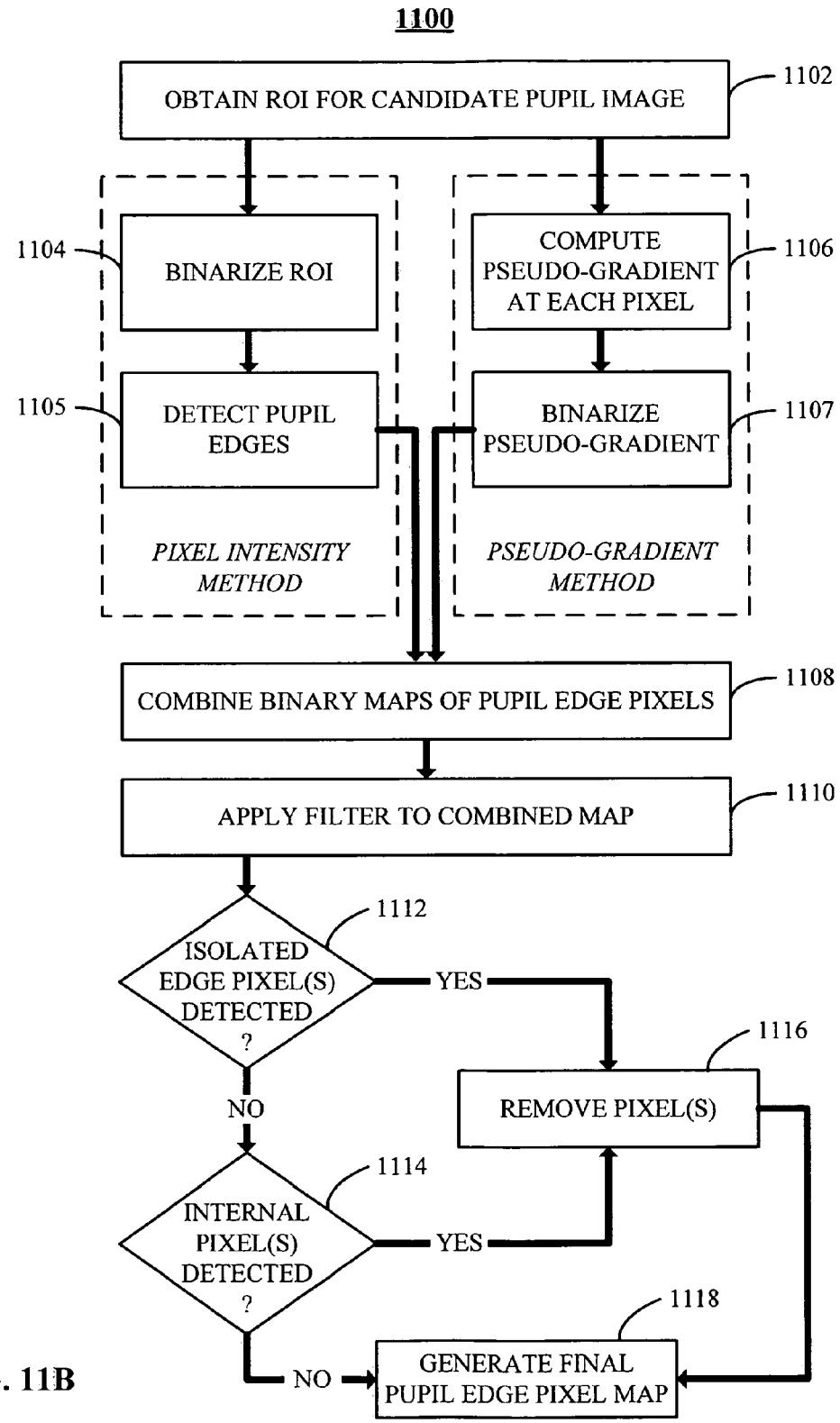
FIG. 11B is a flowchart illustrating a process engaged by the photorefraction ocular screening device using the dual-method binarization approach of FIG. 11A, and corresponding

The ROI for a pupil candidate may be binarized, at step 914, to identify pupil edge pixels. A dual-method approach comprising a pixel intensity method and a pseudo-gradient method, as illustrated in FIG. 11A, may be used to binarize the ROI, each method yielding a binary map of pupil edge pixels. The dual-method approach is described with reference to the flowchart illustrated in FIG. 11B, which provides a pupil edge identification process 1100 employing both the pixel intensity method and the pseudo-gradient method. Process 1100 is initiated by obtaining, at step 1102, the ROI for a selected pupil candidate. Upon obtaining the ROI for the pupil candidate, both the pixel intensity and the pseudo-gradient methods of process 1100 may be applied.

Figure 11C:
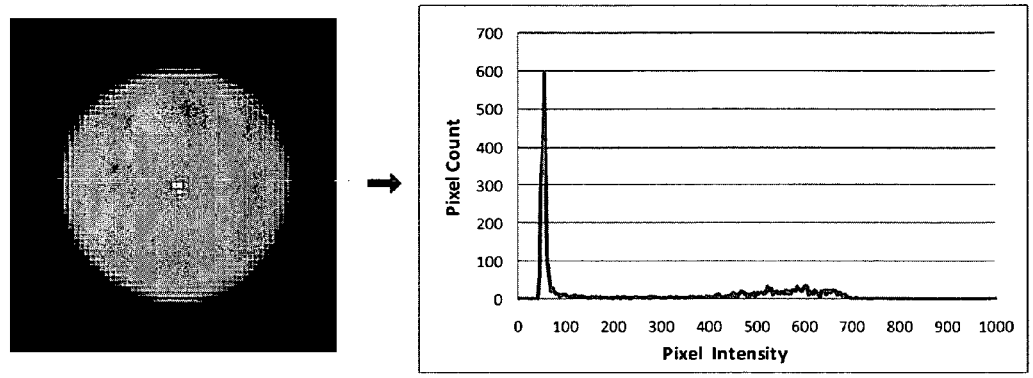
FIGS. 11C-11E illustrate specific aspects of the dual-method binarization approach comprising a pixel intensity method and a pseudo-gradient method, in accordance with embodiments of the present invention.

In the pixel intensity method of process 1100, identifying pupil pixels within a pupil candidate's ROI is accomplished through binarization. The pupil candidate's ROI undergoes binarization, at step 1104, to aid in distinguishing pupil pixels from non-pupil pixels within the ROI. A threshold value is used during binarization and may be determined from an intensity (i.e., brightness) histogram of the ROI. In the ROI, pupil border intensities will be blended with non-pupil pixels, and non-pupil pixels will be darker than pupil pixels. The count of non-pupil pixels in the low intensity part of the histogram will be higher than that of pupil pixels, as illustrated in the intensity histogram of FIG. 11C.

To isolate the pupil point distribution, the intensity with the highest point in the distribution of pixel counts in the lowest approximate 40% of the histogram may be found first and recorded as the median intensity (background) for the area around the pupil. Thereafter, the distribution of pupil points at intensities below the median value may be examined and symmetry on the high side of the median value is assumed to build a distribution associated with the non-pupil points only. The distribution of non-pupil points may then be subtracted from the total distribution to isolate the pupil point distribution only. Any negative pixel counts resulting from the subtraction are set to zero pixel counts, as are all intensities equal to or less than the median. The resultant histogram will be a conservative estimate of intensities in the pupil within the ROI.

Using the resultant histogram, an average pupil intensity value is calculated and the threshold may be set to a mid-point value between the non-pupil median intensity value and the average pupil intensity value. This threshold value is used to generate a binary image of the ROI, wherein pupil intensity values below the threshold value are set to zero and pupil intensity values above or equal to the threshold value are set to one. Pupil edges are then detected, at step 1105, by searching all rows and columns in the generated binary image, proceeding outward from a specified center point (cx,cy) until a non-pupil (zero value) pixel is found. While scanning each row/column, if a pupil pixel does not have an adjacent pupil pixel (non-zero value) in the next row/column, then the edge of the pupil is assumed to be found and the scan in that direction is terminated.

Figure 11D:
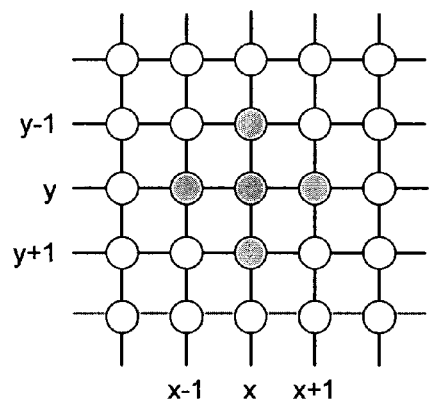

After generating a binary map of edge points using the pixel intensity method, the pseudo-gradient method of process 1100 is employed to generate a second binary map of edge points for a pupil candidate. In the pseudo-gradient method, pupil edge pixels are detected using a rate of change in intensity across an image by computing, at step 1106, a pseudo-gradient at each pixel. Referring to the pixel grid illustrated in FIG. 11D, the pseudo-gradient at a pixel is calculated as follows:

$$Pseudo = \frac{|p(x+1, y) - p(x-1, y)| + |p(x, y+1) - p(x, y-1)|}{2}$$

The pseudo-gradient calculation is as effective as a standard gradient calculation, which is calculated as follows:

$$Gradient = \sqrt{[p(x+1,y) - p(x-1,y)]^2 + [p(x,y+1) - p(x,y-1)]^2}$$

However, using a pseudo-gradient calculation eliminates the need for a computationally expensive square root calculation at each pixel.

Figure 11E:
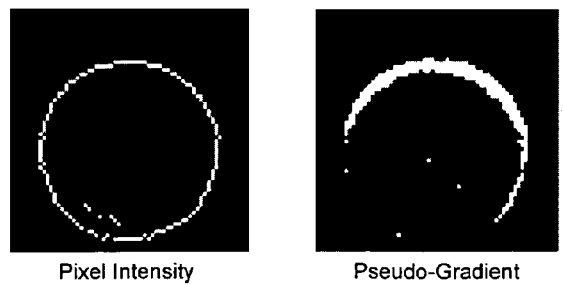

After the pseudo-gradient is calculated at each pixel, the resulting image is subject to binarization, at step 1107, using a threshold value. Here, determination of the threshold value for purposes of binarization is dependent on a result yielded by the pupil intensity method, specifically, the number of edge pixels found in the application of the pixel intensity method. The number of edge pixels yielded by the pixel intensity method may be scaled by four (4), an empirically selected value, and assumed to be the maximum number of edge pixels that can be found using the pseudo-gradient method. Scaling is necessary since the pupil edge yielded by a pseudo-gradient method will not be a clean one-pixel-thick edge, as illustrated in FIG. 11E. Given this maximum number of edge pixels, a search may then be conducted top-down through a pseudo-gradient histogram until the maximum number of edge pixels has been accumulated. The pixel intensity where this occurs may be taken as the threshold value for purposes of binarizing the pseudo-gradient image.

The binary maps yielded by both the pixel intensity and pseudo-gradient methods may be combined, at step 1108, to generate a map of common pupil edge pixels. A filter may then be applied to the map, at step 1110, using a set of predefined criteria to identify undesirable pixel elements. A first determination may be executed, at step 1112, to identify if isolated edge pixel(s) are present. An isolated edge pixel may be a pixel that is not connected to any other edge pixels or it may be a pixel not paired with another edge pixel in its row/column. A second determination may be executed, at step 1114, to identify if internal edge pixel(s) are present. An internal edge pixel may be a pixel that lies between two other pixels in its row/column (e.g., 3 pixels in a row or column). If a determination is made that isolated or internal edge pixels are present, they are removed, at step 1116, and a final pupil edge pixel map is generated, at step 1118.

After the final map is identified, the corresponding pupil edge pixels may be stored, at step 916, and a best-fit circle may be applied, at step 918, using a least squares method. Application of the best-fit circle, using the final pupil edge pixels, identifies the pupil position and size. Various criteria may be used to assess and reject undesirable pupil candidates based on best-fit circle parameters. Pupil candidates may be rejected, for example, if a pupil center is determined to lie outside of the candidate's bounding square, if a pupil diameter is determined to be less than 2 mm or greater than 10 mm, if 12.5% of the filtered edge points are more than ⅓ mm from the circle perimeter, if 50% of the unfiltered edge points are more than ⅓ mm from the circle perimeter, select combinations thereof or any other applicable criteria for determining the suitability of a pupil candidate to undergo refractive error analysis.

Once a pupil candidate has undergone the pupil candidate operations, a determination is made, at step 920 of process 900, whether any pupil candidates remain. If so, the pupil candidate operations returns to the beginning and retrieves, at step 910, the next pupil candidate for binarization and a best-fit circle application. Once all of the pupil candidates have undergone the pupil candidate operations, a refractive error analysis process 1200 may then be executed by processing logic under computer program control in device 100.

Refractive Error Analysis

Refractive error is defined as the optical correction that would provide good vision. In ophthalmology and optometry, optical corrections are almost universally described using three values: a spherical power (sph), a cylindrical power (cyl) and an orientation (axis) for the cylinder. Given an overall refractive state of the eye, the sphere, cylinder and orientation can be used to calculate the refractive error along any meridian of the eye. In photorefraction ocular screening device 100, a reverse method is employed where, given the refractive error along the 0°, 60°, 120° meridians of the eye, these meridional refractive errors can be combined to determine the overall refractive state of the eye. The calculation is comprised of a two-stage process, where intermediate variables A, B and D are determined as follows:

$$A = \frac{r(0°) + r(60°) + r(120°)}{3}$$

$$B = \frac{-2*r(0°) + r(60°) + r(120°)}{3}$$

$$D = \frac{r(60°) - r(120°)}{\sqrt{3}}$$

With values for A, B and D, the overall refractive error is determined using:

$$sph = A - \sqrt{(B^2 + D^2)}$$

$$cyl = 2*\sqrt{(B^2 + D^2)}$$

$$axis = -0.5*\tan^{-1}\left(\frac{D}{B}\right)$$

Once the axis has been calculated, a head-tilt rotation angle may be added to produce the final refractive error.

The pattern of light in a pupil due to the retinal reflection, or reflex, from an eye in response to a NIR LED stimulus is dependent on the refractive state of the eye. In application of NIR LEDs 106b arranged in LED array 106, factors that influence the reflex include the angular position (i.e., the meridians) of NIR LEDs 106b and the perpendicular distance (i.e., the decentration) of NIR LEDs 106b from the central optical axis of image capture component 104. For a given decentration, captured image frames are analyzed to determine the reflexes from patterns of illumination provided along the 0°, 60°, 120° axis lines and, respectively, along their corresponding 180°, 240° and 300° conjugate lines. The results of the two image frames from the axis and conjugate lines along the same meridian may then be combined to determine a refractive power along that meridian.

Figure 12:
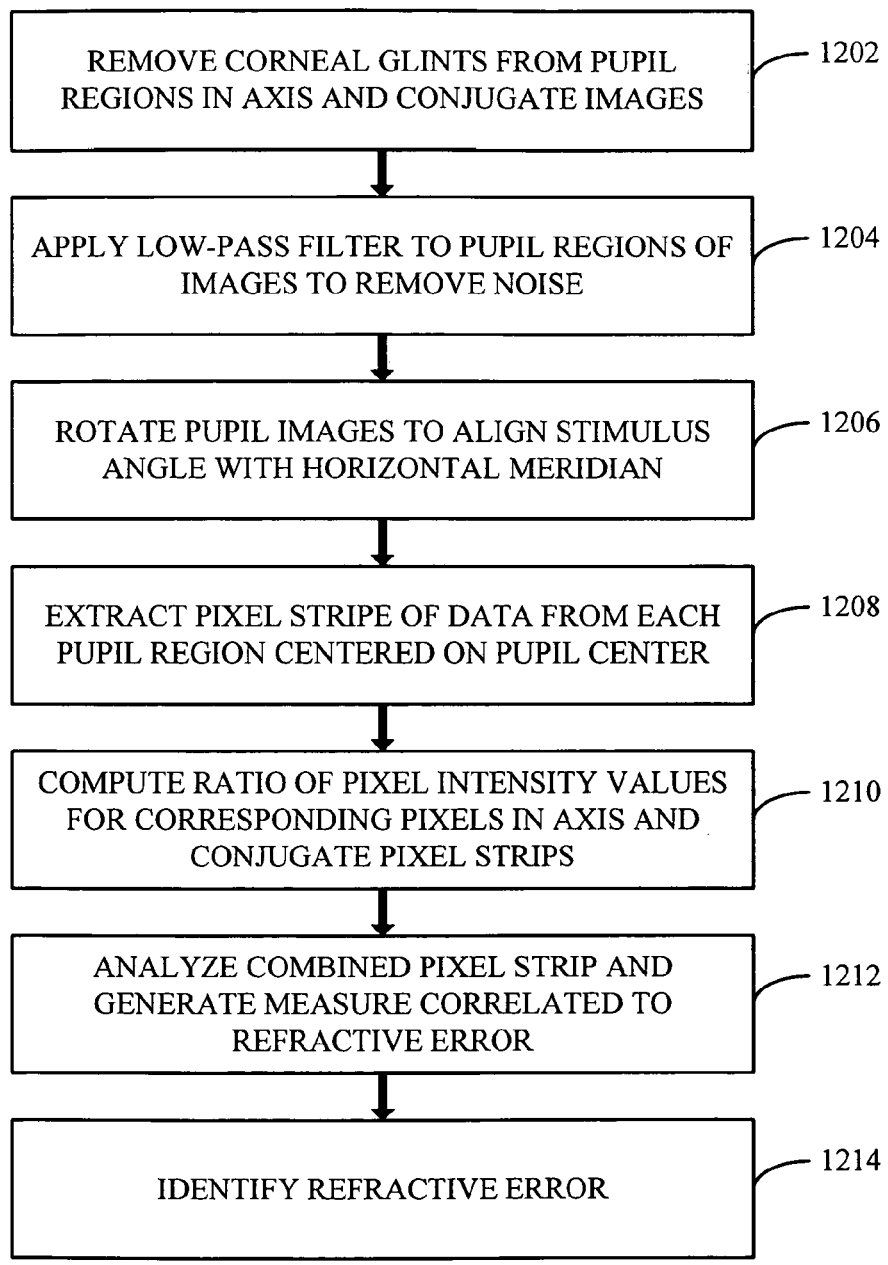
FIG. 12 is a flowchart illustrating a process engaged by the photorefraction ocular screening device for determining refractive error along a meridian, in accordance with embodiments of the present invention.

A process 1200 for determining the refractive power along a meridian is described with reference to the flowchart illustrated in FIG. 12. Process 1200 may be initiated by removal, at step 1202, of corneal glints from pupil regions in the axis and corresponding conjugates images. The glint, which is also commonly referred to as the first Perkinje image or the Hirschberg reflex, is a bright specular reflection of the NIR LEDs from the outer surface of the cornea. Due to the curvature of the cornea, this reflection has a small spatial domain in a well-focused image. To accurately conduct a refractive error determination, the glint must be removed from the pupil reflex. However, the location of the glint relative to the pupil center is retained for calculation of a gaze fixation axis.

If the fixation axis (also called the line of sight) is along the axis which goes through the pupil center and the center of the cornea (i.e., the optical axis), the glint will appear to be in the center of the pupil. If the fixation axis deviates from the optical axis, the glint will appear decentered. One can calculate, to a good approximation, the axis of fixation by the simple relation which states that the eye is rotated by approximately 11.5° per millimeter of decentration (numbers may vary in the literature). Because of the eye's anatomy, it is well established that in a normal gaze position, the fixation axis is not along the optical axis, but rather deviates by approximately 2° to 5° horizontally and 1° to 2° vertically.

In determining the fixation axis, the timing of gaze change, duration of fixation and sequential selections of objects towards which the gaze is directed are not of interest. The sole purposes of monitoring gaze direction are to guarantee that an examinee is looking at the visible attention-getting stimulus (i.e. gaze direction is towards the image capture component 104 of photorefraction ocular screening device 100), and to detect abnormalities in the fixation axis in one or both eyes, which may indicate eye-alignment problems (e.g. strabismus). Any captured image frame in which the gaze direction is not directed at image capture component 104 (e.g. the gaze is directed at the device operator's face) is rejected and not further considered. All measurements depend on acquiring pupil images which evidence a gaze direction towards image capture component 104 within a specified tolerance and allowing for abnormalities.

Figure 13:
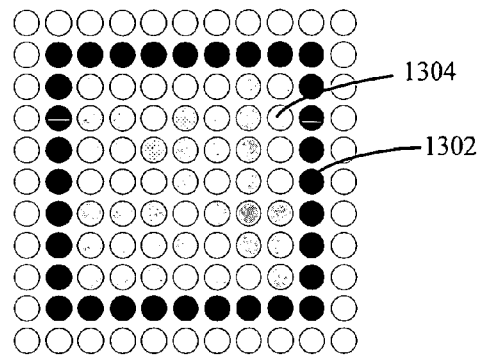
FIG. 13 illustrates a glint interpolation area, in accordance with embodiments of the present invention.

To determine the position of the glint, a 65×65 pixel square may be extracted from around the pupil center. A low pass filter may be applied to this sub-image, wherein the filtered sub-image may then be subtracted from the raw sub-image. The location of the maximum difference resulting from the subtraction of the two images is taken as the center of the glint. Once the center of the glint is identified, new intensity values for pixels surrounding the glint center may then be calculated. A 9×9 surrounding pixel area 1302 may be centered on a glint pixel area 1304, as illustrated in FIG. 13. New intensity values may be calculated using a weighted average of each pixel in area 1302 surrounding area 1304 for glint interpolation. The weight for each pixel in area 1302 may be based on the distance of the pixel from the pixel being interpolated.

Figure 14:
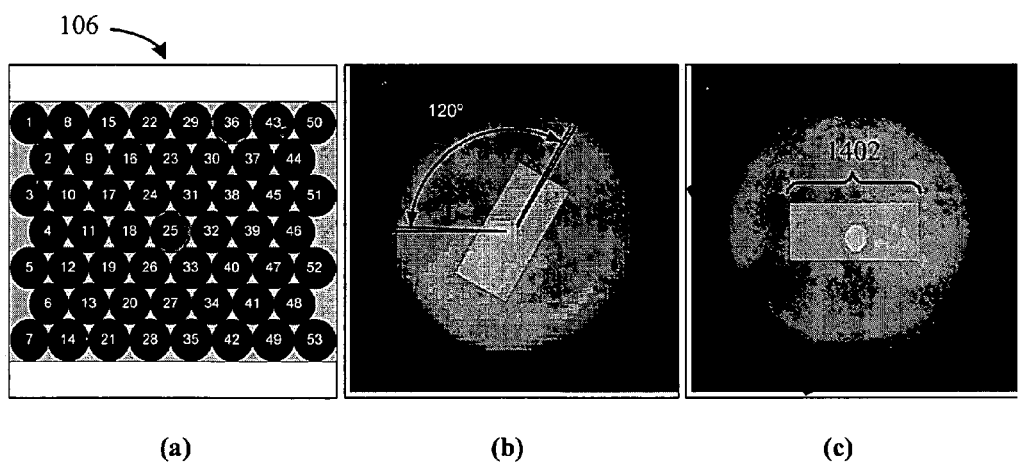
FIG. 14 illustrates rotation of a pixel extraction region, in accordance with embodiments of the present invention.

After removal of the corneal glints, at step 1202, a low-pass filter may be applied, at step 1204, to the pupil region in each image to remove high frequency noise from the reflex data. Once noise is removed from the images, process 1200 may then proceed with executing a rotation, at step 1206, of the pupil images to align stimuli angles with the horizontal meridian. For example, a stimulus decentricity pairing comprising center NIR LED 25 and NIR LED 36, along the axis line of the 60° meridian, is provided by LED array 106, as illustrated in image (a) of FIG. 14. In a preferred embodiment, the pupil image resulting from this stimulus may be rotated counter-clockwise by 120° centered on the pupil center to bring the meridian of interest along the horizontal meridian, as illustrated in image (b) of FIG. 14. This requires the ability to interpolate between pixels to create a rotated image with the same pixel spacing for all axes. Once the image has been rotated, a strip of 25×11 pixels may be extracted, at step 1208, for further processing. A highlighted section 1402, as illustrated in image (c) of FIG. 14, indicates the 25×11 pixel strip that may be used in the analyses. This rotation and extraction process is performed on pupil images in response to stimuli provided on both the axis line and corresponding conjugate line for the same decentration in a selected meridian.

Image ratioing (division) is a technique for feature enhancement using two views of the same object and may be expressed mathematically as:

$$R(i, j) = \frac{V(i, j)_{Axis}}{V(i, j)_{Conjugate}}$$

Where (i,j) are pixel coordinates of input and output images (i.e. pixel by pixel division). Image ratioing is useful for emphasizing the differences between two images, while suppressing similarities. Unlike simple image subtraction, ratioing also cancels out any multiplicative factors (e.g. image sensor gain, exposure time, and magnification due to small distance errors) common to both images.

Figure 15:
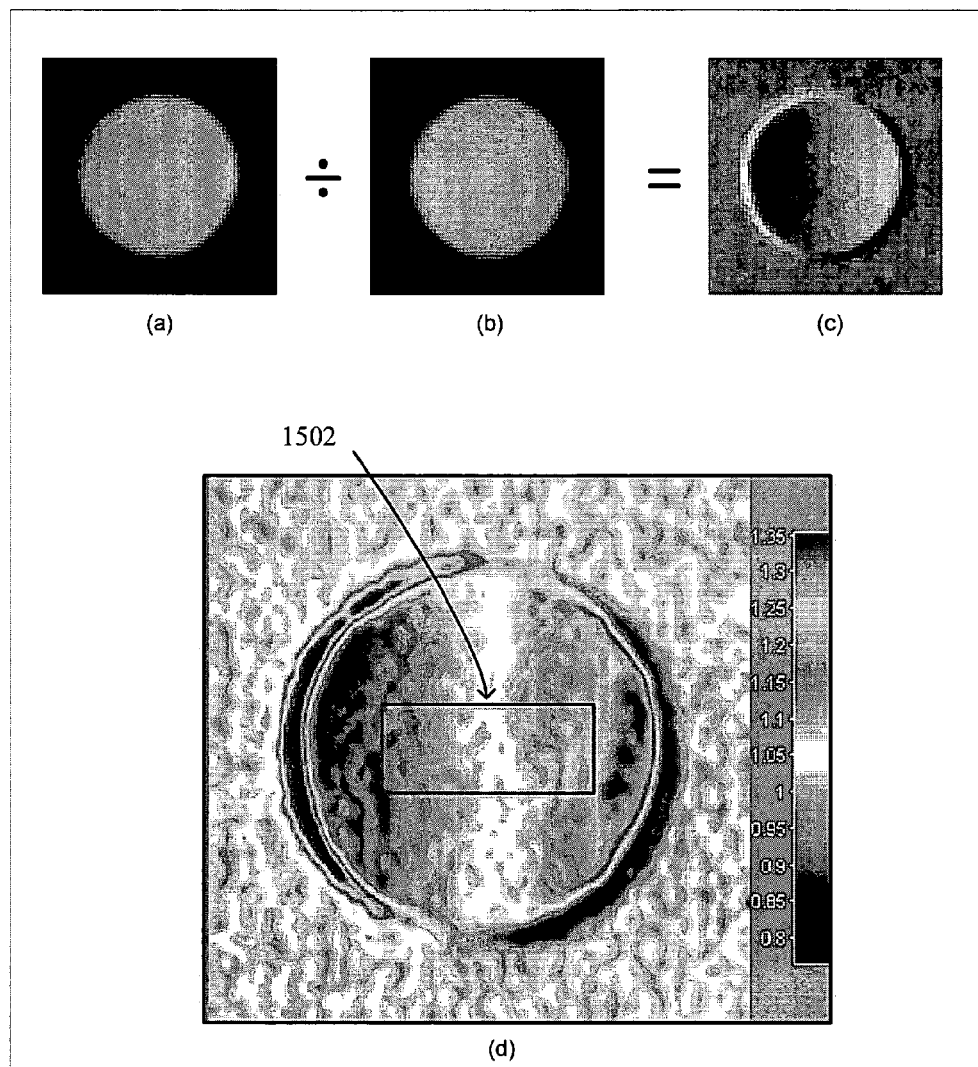
FIG. 15 illustrates pupil image ratioing, in accordance with embodiments of the present invention.

A unique ratioing approach is implemented by the processing logic under computer program control in device 100. In process 1200, the axis and corresponding conjugate images are used as input images, where the ratio of pixel intensity values for the axis and corresponding conjugate pixel strips is computed, at step 1210. An example of the pupil image ratioing in process 1200 is illustrated in FIG. 15, where images (a) and (b) are, respectively, axis and conjugate input images generated in response to a stimulus presented along the 0° meridian at decentrations 12.70 mm from center NIR LED 25 (see FIG. 4B). The result of the ratioing, as illustrated in image (c) of FIG. 15, may be contrast enhanced. A pseudocolor representation, as illustrated in image (d) of FIG. 15, of the resulting ratioing, as illustrated in image (c) of FIG. 15, may also be provided, where an internal rectangle 1502 is representative of the 25×11 pixel strip used in the refractive error analysis.

Figure 16A:
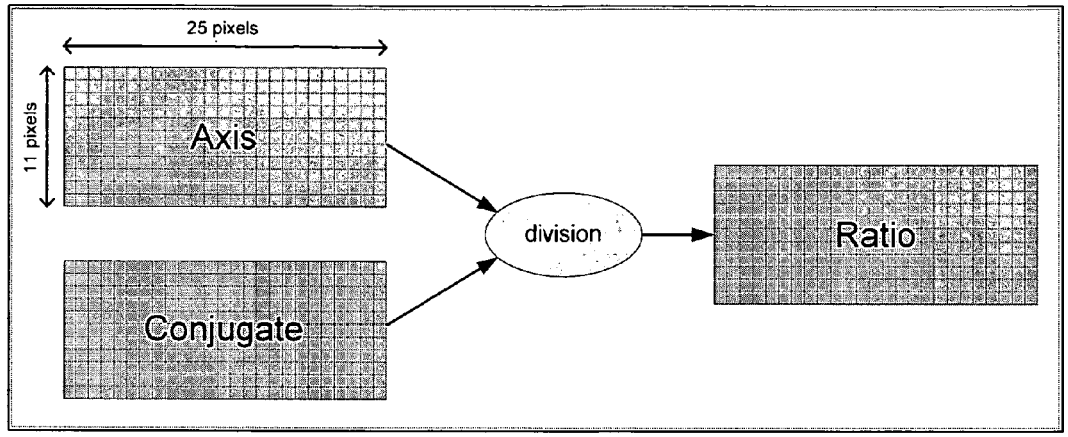
FIGS. 16A-16C illustrate, respectively, computation of an axis-conjugate ratio, generation of a profile slope and generation of a PCA data vector, in accordance with embodiments of the present invention.

As illustrated in FIG. 16A, only the rotated and extracted 25×11 pixel strip pairs from the center of the pupil undergo ratioing. The resulting 25×11 ratio pixel strip is analyzed, at step 1212, to generate a measure that is correlated with refractive error. The analysis at step 1212 may utilize one of two refractive error correlates comprising a profile slope correlate and a principal component analysis (PCA) coefficient correlate.

Figure 16B:
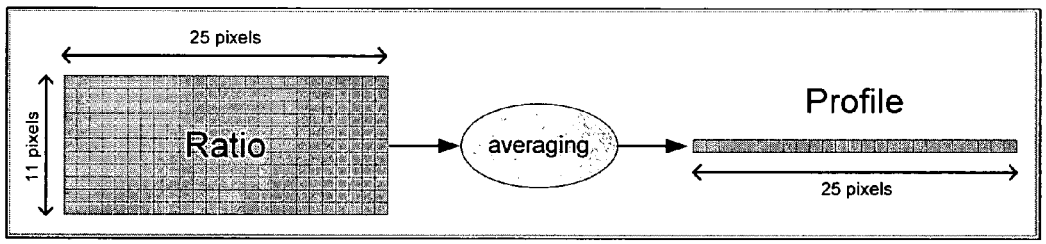
Figure 16C:
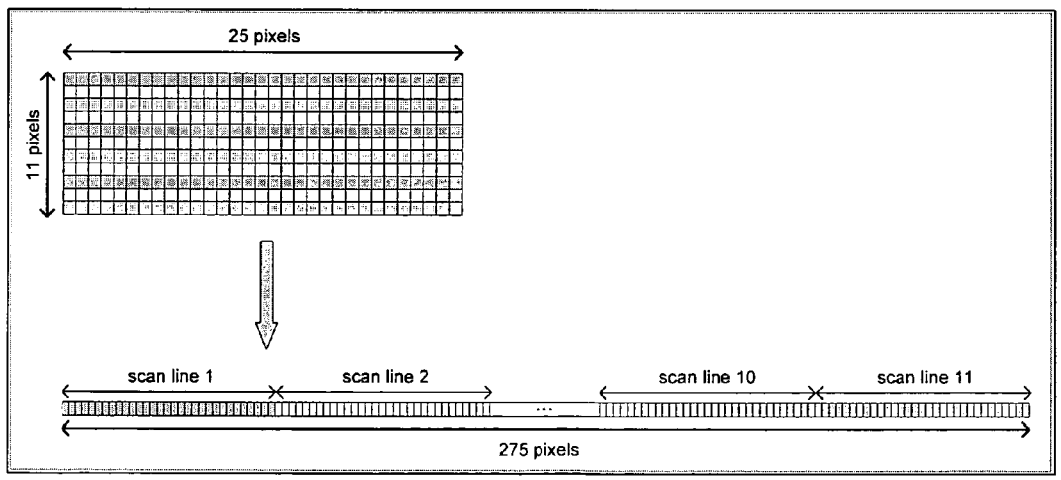

In generating the profile slope correlate, the eleven (11) scan lines of the ratio pixel strip may be averaged, as illustrated in FIG. 16B, to produce a single profile vector that has 25 pixel elements. The slope of the profile vector is computed where y values are the profile values and x values range from −12 to 12 (25 pixels). In generating the PCA coefficient correlate, three (3) vectors are used in its calculation comprising an image data vector, a PCA component vector and a PCA mean vector. Both the PCA component and mean vectors may be predetermined and hard-coded, or loadable, from one or more stored data files accessible by the processing logic under computer program control in device 100. In the PCA coefficient correlate, for ease of calculation, the two-dimensional pixel strip of data is converted to a one-dimensional vector. Transforming the image data grid to a vector, as illustrated in FIG. 16C, creates a vector 275 pixels long, where the first 25 pixels are determined by the first row of data, the next 25 pixels are determined by the second row of data, and so on until all eleven scan lines of the ratio pixel strip are incorporated into the vector.

To calculate the PCA coefficient, the PCA mean factor is first subtracted from the image data vector, as follows:

$$Data_i' = Data_i - Mean_i$$

After the difference is obtained, intermediate sums are computed, as follows:

$$A_{sum} = \sum_i^{275} Component_i$$

$$B_{sum} = \sum_i^{275} Component_i^2$$

Having computed the intermediate sums, the coefficient is calculated as follows:

$$Coefficient = \frac{\left(\sum_i^{275} Data_i' * Component_i\right) - A_{sum} * \left(\sum_i^{275} \frac{Data_i'}{275}\right)}{B_{sum} - \frac{A_{sum}^2}{275}}$$

Conversion of a correlate measure to r(θ), a refractive error in a stimulus meridian angle, may be performed via comparison with a set of decentricity calibration curves. There are total of four (4) curves, D1 through D4, one for each unique decentricity. The decentricities associated with each stimulus meridian are illustrated in FIG. 17A, while sample calibration curves for each of the four decentricities are illustrated in FIG. 17B. The calibration curves may be defined in $\frac{1}{16}^{th}$ diopter steps between −8 and +8 diopters, resulting in 257 elements for each curve. An aggregate error curve may be calculated over this diopter range, as follows:

$$Y_i = \sum_{-8D}^{+8D} \left[(S^{\theta D1} - C_i^{D1})^2 + (S^{\theta D2} - C_i^{D2})^2 + (S^{\theta D3} - C_i^{D3})^2 + (S^{D4} - C_i^{D4})^2\right]$$

where $Y_i$ is the aggregate error value; $S^{\theta D1}$, $S^{\theta D2}$ and $S^{\theta D3}$ are the correlate values along one of three primary stimulus meridian θ at decentricities D1, D2 and D3, respectively; $S^{D4}$ is the average of the correlate values along the 36.59° and 143.41° stimulus meridians at decentricity D4; $C_i^{D1}$, $C_i^{D2}$ and $C_i^{D3}$ are the elements of the calibration curves for decentricities D1, D2 and D3, respectively; and $C_i^{D4}$ are the elements of the calibration curve for decentricity D4. A sample aggregate calibration error curve is illustrated in FIG. 17C. To determine refractive error, at step 1214, the minimum error value is found in the aggregate curve and its associated refractive error is selected.

While the foregoing detailed description illustrates principle embodiments of the invention, it will be appreciated that various modifications can be made by those skilled in the art without departing from the spirit and scope of the invention described herein. The invention can be practiced by other than the described embodiments, which are presented for purposes of illustration and not by way of limitation, and the present invention is limited only by the claims that follow.

What is claimed is:

1. A computer-implemented method of determining refractive error, said method comprising the steps of:
   receiving a first image and a second image corresponding to an axis-conjugate meridian;
   removing corneal glints present in pupil regions of said first image and said second image;
   applying a low-pass filter to each of said pupil regions;
   rotating said first image and said second image, after applying said low-pass filter to said pupil regions in each of said images, to align a stimulus angle in said axis-conjugate meridian associated with said first image and a stimulus angle in said axis-conjugate meridian associated with said second image with a horizontal meridian;
   extracting a pixel strip of data from each of said pupil regions centered on a pupil center in said first image and in said second image;
   computing a ratio of pixel intensity values using said pixel strips of data extracted from said first image and from said second image;
   generating a refractive error correlate measure based on said ratio of pixel intensity values; and
   converting said refractive error correlate measure to identify said refractive error.

2. The method of claim 1, wherein said axis-conjugate meridian is one of three primary axis-conjugate meridians or one of two supplemental axis-conjugate meridians.

3. The method of claim 2, wherein said three primary axis-conjugate meridians are located at a 0° meridian, a 60° meridian and a 120° meridian.

4. The method of claim 3, wherein said 0° meridian includes an axis angle at 0° and a corresponding conjugate angle at 180°, wherein said 60° meridian includes an axis angle at 60° and a corresponding conjugate angle at 240°, and wherein said 120° meridian includes an axis angle at 120° and a corresponding conjugate angle at 300°.

5. The method of claim 4, wherein said axis angle at 0°, said axis angle at 60°, and said axis angle at 120° each has three decentration positions along its axis angle, and
   wherein said corresponding conjugate angle at 180°, said corresponding conjugate angle at 240°, and said corresponding conjugate angle at 300° each has three decentration positions along its conjugate angle.

6. The method of claim 4, wherein said axis angle at 0°, said axis angle at 60°, or said axis angle at 120° is said stimulus angle associated with said first image.

7. The method of claim 4, wherein said corresponding conjugate angle at 180°, said corresponding conjugate angle at 240°, or said corresponding conjugate angle at 300° is said stimulus angle associated with said second image.

8. The method of claim 2, wherein said two supplemental axis-conjugate meridians are located at a 36.59° meridian and a 143.41° meridian.

9. The method of claim 8, wherein said 36.59° meridian includes an axis angle at 36.59° and a corresponding conjugate angle at 216.59°, and wherein said 143.41° meridian includes an axis angle at 143.41° and a corresponding conjugate angle at 323.41°.

10. The method of claim 9, wherein said axis angle at 36.59° or said axis angle at 143.41° is said stimulus angle associated with said first image.

11. The method of claim 9, wherein said corresponding conjugate angle at 216.59° or said corresponding conjugate angle at 323.41° is said stimulus angle associated with said second image.

12. A system employing computer processing logic for determining refractive error, comprising:
   a processor component coupled to at least one memory component, said processor component configured to:
      receive a first image and a second image corresponding to an axis-conjugate meridian;
      remove corneal glints present in pupil regions of said first image and said second image;
      apply a low-pass filter to each of said pupil regions;
      rotate said first image and said second image, after applying said low-pass filter to said pupil regions in each of said images, to align a stimulus angle in said axis-conjugate meridian associated with said first image and a stimulus angle in said axis-conjugate meridian associated with said second image with a horizontal meridian;
      extract a pixel strip of data from each of said pupil regions centered on a pupil center in said first image and in said second image;
      compute a ratio of pixel intensity values using said pixel strips of data extracted from said first image and from said second image;
      generate a refractive error correlate measure based on said ratio of pixel intensity values; and
      convert said refractive error correlate measure to identify said refractive error.

13. A non-transitory computer-readable storage medium programmed to include instructions that, when executed by a processor, cause the processor to perform a method for determining refractive error, said method comprising the steps of:
   receiving a first image and a second image corresponding to an axis-conjugate meridian;
   removing corneal glints present in pupil regions of said first image and said second image;
   applying a low-pass filter to each of said pupil regions;
   rotating said first image and said second image, after applying said low-pass filter to said pupil regions in each of said images, to align a stimulus angle in said axis-conjugate meridian associated with said first image and a stimulus angle in said axis-conjugate meridian associated with said second image with a horizontal meridian;
   extracting a pixel strip of data from each of said pupil regions centered on a pupil center in said first image and in said second image;
   computing a ratio of pixel intensity values using said pixel strips of data extracted from said first image and from said second image;
   generating a refractive error correlate measure based on said ratio of pixel intensity values; and
   converting said refractive error correlate measure to identify said refractive error.

* * * * *